United States Patent
Zhang

(10) Patent No.: US 11,998,553 B2
(45) Date of Patent: Jun. 4, 2024

(54) CERTAIN (2S)-N-[(1S)-1-CYANO-2-PHENYLETHYL]-1,4-OXAZEPANE-2-CARBOXAMIDES FOR TREATING LUPUS NEPHRITIS

(71) Applicant: Insmed Incorporated, Bridgewater, NJ (US)

(72) Inventor: Jimin Zhang, Bridgewater, NJ (US)

(73) Assignee: Insmed Incorporated, Bridgewater, NJ (US)

( * ) Notice: Subject to any disclaimer, the term of this patent is extended or adjusted under 35 U.S.C. 154(b) by 638 days.

(21) Appl. No.: 17/260,606

(22) PCT Filed: Jul. 16, 2019

(86) PCT No.: PCT/US2019/042021
§ 371 (c)(1),
(2) Date: Jan. 15, 2021

(87) PCT Pub. No.: WO2020/018547
PCT Pub. Date: Jan. 23, 2020

(65) Prior Publication Data
US 2021/0322438 A1    Oct. 21, 2021

Related U.S. Application Data

(60) Provisional application No. 62/699,494, filed on Jul. 17, 2018.

(51) Int. Cl.
| A61K 31/553 | (2006.01) |
| A61K 31/52 | (2006.01) |
| A61K 31/5377 | (2006.01) |
| A61K 45/06 | (2006.01) |
| A61P 13/12 | (2006.01) |

(52) U.S. Cl.
CPC ........... *A61K 31/553* (2013.01); *A61K 31/52* (2013.01); *A61K 31/5377* (2013.01); *A61K 45/06* (2013.01); *A61P 13/12* (2018.01)

(58) Field of Classification Search
CPC .. A61K 31/553; A61K 31/52; A61K 31/5377; A61K 45/06; A61P 13/12
USPC .................................................. 514/211.15
See application file for complete search history.

(56) References Cited

U.S. PATENT DOCUMENTS

| 8,552,034 B2 | 10/2013 | Verwijs et al. |
| 8,871,783 B2 | 10/2014 | Anderskewitz et al. |
| 8,877,775 B2 | 11/2014 | Anderskewitz et al. |
| 8,889,708 B2 | 11/2014 | Grauert et al. |
| 8,987,249 B2 | 3/2015 | Anderskewitz et al. |
| 8,999,975 B2 | 4/2015 | Grundl et al. |
| 9,073,869 B2 | 7/2015 | Anderskewitz et al. |
| 9,440,960 B2 | 9/2016 | Grauert et al. |
| 9,522,894 B2 | 12/2016 | Lonn et al. |
| 9,713,606 B2 | 7/2017 | Anderskewitz et al. |
| 9,815,805 B2 | 11/2017 | Lonn et al. |
| 9,856,228 B2 | 1/2018 | Lauritzen et al. |
| 9,879,026 B2 | 1/2018 | Vintonyak et al. |
| 10,238,633 B2 | 3/2019 | Anderskewitz et al. |
| 10,287,258 B2 | 5/2019 | Lonn et al. |
| RE47,636 E | 10/2019 | Vintonyak et al. |
| 10,479,781 B2 | 11/2019 | Lauritzen et al. |
| 10,669,245 B2 | 6/2020 | Lonn et al. |
| 11,117,874 B2 | 9/2021 | Lonn et al. |
| 11,655,221 B2 | 5/2023 | Lönn et al. |
| 11,655,222 B2 | 5/2023 | Lönn et al. |
| 11,655,223 B2 | 5/2023 | Lönn et al. |
| 11,655,224 B2 | 5/2023 | Lönn et al. |
| 11,667,615 B2 | 6/2023 | Lonn et al. |
| 11,673,871 B2 | 6/2023 | Lönn et al. |
| 11,673,872 B2 | 6/2023 | Lönn et al. |
| 11,680,049 B2 | 6/2023 | Lönn et al. |

(Continued)

FOREIGN PATENT DOCUMENTS

| CN | 101945851 A | 1/2011 |
| CN | 102574830 A | 7/2012 |

(Continued)

OTHER PUBLICATIONS

Alpsoy E., "Behcet's Disease: Treatment of Mucocutaneous Lesions," Clinical and Experimental Rheumatology, Apr. 2005, vol. 23, No. 4, pp. 532-539.

(Continued)

*Primary Examiner* — Kristin A Vajda
(74) *Attorney, Agent, or Firm* — COOLEY LLP

(57) ABSTRACT

The present disclosure relates to methods for treating lupus nephritis with compositions comprising an effective amount of certain (2S)-N-[(1S)-1-cyano-2-phenylethyl]-1,4-oxazepane-2-carboxamide compounds of Formula (I), including pharmaceutically acceptable salts thereof, that inhibit dipeptidyl peptidase 1 (DPP1) activity. In one embodiment, the compound of Formula (I) is (2S)-N-{(1S)-1-cyano-2-[4-(3-methyl-2-oxo-2,3-dihydro-1,3-benzoxazol-5-yl)phenyl]ethyl}-1,4-oxazepane-2-carboxamide (INS1007).

(I)

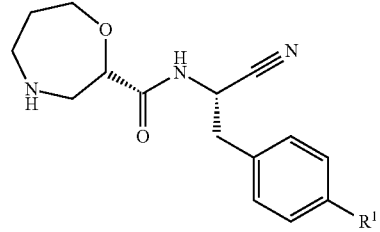

20 Claims, 9 Drawing Sheets

(56) References Cited

U.S. PATENT DOCUMENTS

| | | |
|---|---|---|
| 11,773,069 B2 | 10/2023 | Lönn et al. |
| 11,814,359 B2 | 11/2023 | Lönn et al. |
| 2008/0221093 A1 | 9/2008 | Gege et al. |
| 2012/0315271 A1 | 12/2012 | Shelton et al. |
| 2012/0329775 A1 | 12/2012 | Ford et al. |
| 2014/0275159 A1 | 9/2014 | Anderskewitz et al. |
| 2015/0025058 A1 | 1/2015 | Deutsch et al. |
| 2015/0105375 A1 | 4/2015 | Anderskewitz et al. |
| 2015/0210655 A1 | 7/2015 | Lonn et al. |
| 2015/0224199 A1 | 8/2015 | De Weer et al. |
| 2015/0346203 A1 | 12/2015 | Xu et al. |
| 2016/0061824 A1 | 3/2016 | Hahn et al. |
| 2016/0324854 A1 | 11/2016 | Finnie et al. |
| 2017/0027907 A1 | 2/2017 | Legangneux et al. |
| 2017/0057938 A1 | 3/2017 | Lonn et al. |
| 2018/0028541 A1 | 2/2018 | Lonn et al. |
| 2018/0044328 A1 | 2/2018 | Lauritzen et al. |
| 2018/0169017 A1 | 6/2018 | Desai et al. |
| 2018/0251436 A1 | 9/2018 | Lonn et al. |
| 2019/0091236 A1 | 3/2019 | Lonn et al. |
| 2019/0167636 A1 | 6/2019 | Anderskewitz et al. |
| 2019/0247400 A1 | 8/2019 | Dipetrillo et al. |
| 2020/0017455 A1 | 1/2020 | Lonn et al. |
| 2020/0138780 A1 | 5/2020 | Anderskewitz et al. |
| 2020/0179398 A1 | 6/2020 | Lonn et al. |
| 2020/0247765 A1 | 8/2020 | Lonn et al. |
| 2020/0256866 A1 | 8/2020 | Tirouvanziam |
| 2020/0390781 A1 | 12/2020 | Dipetrillo et al. |
| 2021/0186931 A1 | 6/2021 | Davidson et al. |
| 2021/0186984 A1 | 6/2021 | Dipetrillo et al. |
| 2021/0238152 A1 | 8/2021 | Lonn et al. |
| 2021/0252015 A1 | 8/2021 | Zhang |
| 2021/0369732 A1 | 12/2021 | Wikstrom et al. |
| 2022/0133737 A1 | 5/2022 | Lonn et al. |
| 2023/0025351 A1 | 1/2023 | Lönn et al. |
| 2023/0028726 A1 | 1/2023 | Lönn et al. |
| 2023/0033573 A1 | 2/2023 | Lönn et al. |
| 2023/0062646 A1 | 3/2023 | Lönn et al. |
| 2023/0069044 A1 | 3/2023 | Lönn et al. |
| 2023/0085620 A1 | 3/2023 | Lönn et al. |
| 2023/0115170 A1 | 4/2023 | Lönn et al. |
| 2023/0116721 A1 | 4/2023 | Lönn et al. |
| 2023/0250071 A1 | 8/2023 | Lönn et al. |
| 2023/0278969 A1 | 9/2023 | Lönn et al. |

FOREIGN PATENT DOCUMENTS

| | | |
|---|---|---|
| CN | 112920124 A | 6/2021 |
| EP | 1317555 B1 | 11/2007 |
| EP | 2840083 A1 | 2/2015 |
| JP | 2006527704 A | 12/2006 |
| JP | 2008501692 A | 1/2008 |
| JP | 2008504307 A | 2/2008 |
| JP | 2010540526 A | 12/2010 |
| JP | 2011506421 A | 3/2011 |
| JP | 2011522011 A | 7/2011 |
| JP | 2012522764 A | 9/2012 |
| JP | 2012526093 A | 10/2012 |
| JP | 2016515576 A | 5/2016 |
| JP | 2017503832 A | 2/2017 |
| JP | 2019070029 A | 5/2019 |
| JP | 2021046423 A | 3/2021 |
| TW | 201041889 A | 12/2010 |
| WO | WO 1999/017777 | 4/1999 |
| WO | WO 2001/016108 | 3/2001 |
| WO | WO 2001/096285 | 12/2001 |
| WO | WO 2002/051831 | 7/2002 |
| WO | WO 2003/048123 | 6/2003 |
| WO | WO-2004076434 A1 | 9/2004 |
| WO | WO 2004/087153 | 10/2004 |
| WO | WO 2004/110988 | 12/2004 |
| WO | WO-2004106289 A1 | 12/2004 |
| WO | WO 2005/107762 | 11/2005 |
| WO | WO-2005106012 A2 | 11/2005 |
| WO | WO-2005120465 A2 | 12/2005 |
| WO | WO-2006000228 A2 | 1/2006 |
| WO | WO 2006/020145 | 2/2006 |
| WO | WO 2007/005668 | 1/2007 |
| WO | WO 2008/109180 | 9/2008 |
| WO | WO 2008/109181 | 9/2008 |
| WO | WO 2009/026701 | 3/2009 |
| WO | WO-2009042187 A1 | 4/2009 |
| WO | WO 2009/074829 | 6/2009 |
| WO | WO-2009147238 A1 | 12/2009 |
| WO | WO 2010/077680 | 7/2010 |
| WO | WO-2010114405 A2 | 10/2010 |
| WO | WO 2010/128324 | 11/2010 |
| WO | WO 2010/142985 | 12/2010 |
| WO | WO 2011/154677 | 12/2011 |
| WO | WO 2012/064715 | 5/2012 |
| WO | WO 2012/119941 | 9/2012 |
| WO | WO 2013/041497 | 3/2013 |
| WO | WO 2014/091443 | 6/2014 |
| WO | WO 2014/140075 | 9/2014 |
| WO | WO 2014/140081 | 9/2014 |
| WO | WO 2014/140091 | 9/2014 |
| WO | WO 2014/151784 | 9/2014 |
| WO | WO-2014165303 A1 | 10/2014 |
| WO | WO 2015/032942 | 3/2015 |
| WO | WO 2015/032943 | 3/2015 |
| WO | WO 2015/032945 | 3/2015 |
| WO | WO 2015/110826 | 7/2015 |
| WO | WO-2015175939 A1 | 11/2015 |
| WO | WO 2016/075240 | 5/2016 |
| WO | WO 2018/022978 | 2/2018 |
| WO | WO 2019/157050 | 8/2019 |
| WO | WO-2019166626 A1 | 9/2019 |
| WO | WO 2020/018547 | 1/2020 |
| WO | WO 2020/018551 | 1/2020 |
| WO | WO-2020247665 A1 | 12/2020 |
| WO | WO-2022140516 A1 | 6/2022 |
| WO | WO-2022232420 A1 | 11/2022 |
| WO | WO-2022232573 A1 | 11/2022 |
| WO | WO-2023076615 A1 | 5/2023 |
| WO | WO-2023159120 A1 | 8/2023 |

OTHER PUBLICATIONS

Avci, D., "Dipeptidyl Peptidase-4 Inhibitors and Inflammation: Dpp-4 Inhibitors Improve Mean Pleatelet Volume and Gamma Glutamyl Transferase Level," Journal of Biosciences and Medicines, vol. 7, No. 2, Feb. 2019, pp. 42-53.

Bae, S. et al., "Elevated interleukin-32 expression in granulomatosis with polyangiitis," Rheumatology 2012;51:1979-1988, doi:10.1093/rheumatology/kes163, Advance Access publication Jul. 31, 2012.

Chalmers, J. D. et al., "The Bronchiectasis Severity Index. An International Derivation and Validation Study," Am. J. Respir. Crit. Care Med., Mar. 2014; 189(5):576-585.

Everts-Graber, J. et al., "Proteomic analysis of neutrophils in ANCA-associated vasculitis reveals a dysregulation in proteinase 3-associated proteins such as annexin-A1 involved in apoptotic cell clearance," Kidney International (2019) 96, 397-408; https://doi.org/10.1016/j.kint.2019.02.017.

Extended European Search Report for European Application No. 19751012.6, dated Oct. 4, 2021, 7 pages.

Extended European Search Report for European Application No. 19837016.5, dated Mar. 18, 2022, 10 pages.

Goeminne, P. C. et al., "Mortality in non-cystic fibrosis bronchiectasis: A prospective cohort analysis," Respir. Med., Feb. 2014; 108(2):287-296.

International Search Report and Written Opinion for International Application No. PCT/US2021/064810, dated Mar. 16, 2022, 8 pages.

Jones, B. E. et al., "Gene-Specific DNA Methylation Changes Predict Remission in Patients with ANCA-Associated Vasculitis," J Am Soc Nephrol 28: 1175-1187, 2017. doi: 10.1681/ASN.2016050548.

Kelly, M. G. et al., "Bronchiectasis in secondary care: A comprehensive profile of a neglected disease," Eur. J. Intern. Med., Sep. 2003; 14(8): 488-492.

(56) References Cited

OTHER PUBLICATIONS

Schreiber, A. et al., "Neutrophil serine proteases promote IL-1β generation and injury in necrotizing crescentic glomerulonephritis," Journal of the American Society of Nephrology, vol. 23, No. 3, Mar. 2012, pp. 470-482.
Extended European Search Report for European Application No. 19838400.0, dated Mar. 24, 2022, 9 pages.
Golchert, D. et al. (Sep. 2013), "Evaluation of some compression aids in tableting of roller compacted swellable core drug layer," Int J Pharm., 453(2):322-328.
International Search Report and Written Opinion for International Application No. PCT/US2022/026769, dated Sep. 9, 2022, 15 pages.
International Search Report and Written Opinion for International Application No. PCT/US2022/027026, dated Sep. 14, 2022, 11 pages.
Invitation to Pay Additional Fees for International Application No. PCT/US2022/026769, dated Jun. 27, 2022, 3 pages.
Invitation to Pay Additional Fees for International Application No. PCT/US2022/027026, dated Jul. 8, 2022, 2 pages.
Karthik, V. V. (Jun. 2016), "Excipients Used in the Formulation of Tablets," RRJCHEM, 5(2):143-154.
Kono, H., et al. (Oct. 2012), "The IL-1-dependent sterile inflammatory response has a substantial caspase-1-independent component that requires cathepsin C," The Journal of Immunology, vol. 189, No. 7, pp. 3734-3740.
U.S. National Library of Medicine, "Randomized, Double-Blind, Placebo-Controlled, Parallel-Group, Multi-Center Study of Efficacy, Safety & Tolerability, and Pharmacokinetics of INS1007 Administered Daily for 24 Weeks in Non-Cystic Fibrosis Bronchiectasis—The Willow Study," Study NCT03218917 [online], Retrieved from the Internet: <https://clinicaltrials.gov/ct2/history/NCT03218917?V_1=View#StudyPageTop>, Jul. 2017, 8 pages.
International Search Report and Written Opinion for International Application No. PCT/US2017/044343, dated Oct. 12, 2017, 7 pages.
Extended European Search Report for European Application No. 17835331.4, dated Feb. 11, 2020, 8 pages.
International Search Report and Written Opinion for International Application No. PCT/GB2015/050155, dated Mar. 6, 2015, 7 pages.
Extended European Search Report for European Application No. 17195612.1, dated Mar. 21, 2018, 5 pages.
Extended European Search Report for European Application No. 20173862.2, dated Sep. 11, 2020, 7 pages.
International Search Report and Written Opinion for International Application No. PCT/EP2019/055138, dated Jul. 19, 2019, 11 pages.
International Search Report and Written Opinion for International Application No. PCT/US2019/016844, dated May 31, 2019, 10 pages.
International Search Report and Written Opinion for International Application No. PCT/US2019/042026, dated Sep. 4, 2019, 7 pages.
International Search Report and Written Opinion for International Application No. PCT/US2019/042021, dated Sep. 4, 2019, 7 pages.
Pubchem, CID 134527801, "(2S)-2-[[Hydroxy-[(2S)-1,4-oxazepan-2-yl]methyl]amino]-3-[4-(3-methyl-2-oxo-1,3-benzoxazol-5-yl)phenyl]propanenitrile," Jun. 23, 2018, Retrieved from the Internet: <URL: https://pubchem.ncbi.nlm.nih.gov/compound/134527801>, 6 pages.
Birring, S. S. et al., "Development of a symptom specific health status measure for patients with chronic cough: Leicester Cough Questionnaire (LCQ)," Thorax 2003; 58:339-343.
Bondebjerg, J. et al., "Dipeptidyl nitriles as human dipeptidyl peptidase I inhibitors," Bioorganic & Medicinal Chemistry Letters, vol. 16, No. 13, pp. 3614-3617 (2006).
Doyle, K. et al., "Discovery of second generation reversible covalent DPP1 inhibitors leading to an Oxazepane Amidoacetonitrile based clinical candidate (AZD7986)," Journal of Medicinal Chemistry, 59(20):9457-9472 (Oct. 2016).

Furber, M. et al., "Cathepsin C Inhibitors: Property Optimization and Identification of a Clinical Candidate," Journal of Medicinal Chemistry, 2014, vol. 57, pp. 2357-2367.
Miller, M. R. et al., "Standardisation of spirometry," Eur. Respir. J. 2005; 26:319-338.
Murray, M. P. et al., "Sputum colour: a useful clinical tool in non-cystic fibrosis bronchiectasis," Eur Respir J 2009; 34: 361-364.
Murray, M. P. et al., "Validation of the Leicester Cough Questionnaire in non-cystic fibrosis bronchiectasis," Eur Respir J 2009; 34: 125-131.
Stenton, C., "The MRC breathlessness scale," Occupational Medicine 2008; 58:226-227.
Stockley, R. et al., "Phase II study of a neutrophil elastase inhibitor (AZD9668) in patients with bronchiectasis," Respiratory Medicine, vol. 107, No. 4, Feb. 2013, pp. 524-533.
Korkmaz, B. et al., "Neutrophil Elastase, Proteinase 3, and Cathepsin G as Therapeutic Targets in Human Diseases," Pharmacological Reviews, vol. 62, No. 4, Nov. 2010, pp. 726-759.
Wickremasinghe, M. et al., "Non-tuberculous mycobacteria in patients with bronchiectasis," Thorax, 60(12):1045-1051 (2005).
Bragg, R. A. et al., "Aortic Binding of AZD5248: Mechanistic Insight and Reactivity Assays to Support Lead Optimization," Chem Res Toxicol. Oct. 19, 2015;28(10):1991-1999. doi: 10.1021/acs.chemrestox.5b00236. Epub Sep. 16, 2015.
Adkison, A. M. et al., "Dipeptidyl peptidase I activates neutrophil-derived serine proteases and regulates the development of acute experimental arthritis," J. Clin. Invest. 109(3):363-371 (2002).
Suppiah, R. et al., "A cross-sectional study of the Birmingham Vasculitis Activity Score version 3 in systemic vasculitis," Rheumatology 2011;50:899-905.
Floris, A. et al., "Using the Birmingham vasculitis activity score as a screening tool in patients with suspected vasculitis," i174, Apr. 28, 2016, Poster Viewing III, Retrieved from the Internet: <URL: https://academic.oup.com/rheumatology/article-abstract/55/suppl_1/i174/1795586>, Retrieved from the Internet on Apr. 23, 2018, 1 page.
Birmingham Vasculitis Activity Score (version 3), 1 page [No Date].
Cartin-Ceba, R. et al., "Rituximab for Remission Induction and Maintenance in Refractory Granulomatosis With Polyangiitis (Wegener's)," Arthritis & Rheumatism, vol. 64, No. 11, Nov. 2012, pp. 3770-3778.
Dadoniene, J. et al., "Clinical characteristics and long-term survival differences of the ANCA-associated vasculitis group: a cross-sectional study of 27 patients," ACTA Medica Lituanica, 2017, vol. 24, No. 2, pp. 107-112.
Geetha, D. et al., "Current therapy of granulomatosis with polyangiitis and microscopic polyangiitis: the role of rituximab," J Nephrol (2015) 28:17-27.
Guillevin, L. et al., "Microscopic Polyangiitis," Arthritis & Rheumatism, vol. 42, No. 3, Mar. 1999, pp. 421-430.
Insmed, "Insmed Announces Positive Top-Line Results from Phase 2 WILLOW Study of INS1007 in Patients with Non-Cystic Fibrosis Bronchiectasis," Feb. 3, 2020, 5 pages.
Jarrot, P-A et al., "Review Pathogenesis of ANCA-associated vasculitis: An update," Autoimmunity Reviews, vol. 15, Issue 7, Jul. 2016, pp. 704-713.
Jenne, D. E., "Wegener's autoantigen decoded," Nature, vol. 346, Aug. 9, 1990, p. 520.
Jennette, J. C., "Nomenclature and classification of vasculitis: lessons learned from granulomatosis with polyangiitis (Wegener's granulomatosis)," Clinical and Experimental Immunology, 164 (Suppl. 1), 7-10 (2011).
Kallenberg, C. G. M. et al., "Mechanisms of Disease: pathogenesis and treatment of ANCA-associated vasculitides," Nature Clinical Practice Rheumatology, Dec. 2006, vol. 2, No. 12, pp. 661-670.
Keogh, K. A. et al., "Rituximab for Refractory Wegener's Granulomatosis. Report of a Prospective, Open-Label Pilot Trial," Am J Respir Crit Care Med vol. 173. pp 180-187 (2006).
Kettritz, R., "Autoimmunity in kidney diseases," The Scandinavian Journal of Clinical & Laboratory Investigation, vol. 68, No. S241, Jun. 2008, 99-103.

(56) References Cited

OTHER PUBLICATIONS

Knopf, A. et al., "Clinical aspects of granulomatosis with polyangiitis affecting the head and neck," Eur Arch Otorhinolaryngol (2015) 272:185-193.
Korkmaz, B. et al., "Neutrophil proteinase 3 and dipeptidyl peptidase I (cathepsin C) as pharmacological targets in granulomatosis with polyangiitis (Wegener granulomatosis)," Semin Immunopathol (2013) 35:411-421.
Lins, L. et al., "SF-36 total score as a single measure of health-related quality of life: Scoping review," SAGE Open Medicine, vol. 4:1-12 (2016).
Luqmani, R. A. et al., "Birmingham Vasculitis Activity Score (BVAS) in Systemic Necrotizing Vasculitis," Q. J. Med. 1994; 87:671-678.
Mukhtyar, C. et al., "Modification and validation of the Birmingham Vasculitis Activity Score (version 3)," Ann Rheum Dis 2009;68:1827-1832.
Pagnoux, C. et al., "Optimal therapy and prospects for new medicines in eosinophilic granulomatosis with polyangiitis (Churg-Strauss syndrome)," Expert Review of Clinical Immunology, vol. 12, No. 10, pp. 1059-1067 (2016).
Pagnoux, C. et al., "Treatment of granulomatosis with polyangiitis (Wegener's)," Expert Review of Clinical Immunology, 11:3, 339-348 (2015).
Falk, R. J. et al., "Anti-neutrophil cytoplasmic autoantibodies induce neutrophils to degranulate and produce oxygen radicals in vitro," Proc. Natl. Acad. Sci. USA, vol. 87, pp. 4115-4119, Jun. 1990.
Popa, E. R. et al., "Differential B- and T-cell activation in Wegener's granulomatosis," J Allergy Clin Immunol 1999;103:885-894.
Rawn, S. et al., "Purpura, petechiae, and bullae as first signs of juvenile granulomatosis with polyangiitis," Eur J Pediatr (2014) 173:1685-1689.
Selga, D. et al., "Polyarteritis nodosa when applying the Chapel Hill nomenclature—a descriptive study on ten patients," Rheumatology 2006;45:1276-1281.
Shapiro, S. C. et al., "Inflammatory bowel disease mimicking granulomatosis with polyangiitis: a case report," Journal of Medical Case Reports (2016) 10:214.
Schirmer, J. H. et al., "Clinical presentation and long-term outcome of 144 patients with microscopic polyangiitis in a monocentric German cohort," Rheumatology 2016;55:71-79.
Stone, J. H. et al., "A Disease-Specific Activity Index for Wegener's Granulomatosis, " Arthritis & Rheumatism, vol. 44, No. 4, Apr. 2001, pp. 912-920.
Suka, M. et al., "Improvement in health-related quality of life in MPO-ANCA-associated vasculitis patients treated with cyclophosphamide plus prednisolone: an analysis of 18 months of follow-up data from the JMAAV study," Mod Rheumatol (2012) 22:877-884.
Trouvin, A.-P. et al., "Usefulness of monitoring of B cell depletion in rituximab-treated rheumatoid arthritis patients in order to predict clinical relapse: a prospective observational study," Clinical and Experimental Immunology, 180: 11-18 (2014).
Von Vietinghoff, S. et al., "Membrane proteinase 3 and Wegener's granulomatosis," Clinical Nephrology, vol. 64, No. 4, pp. 453-459 (2005).
Yates, M. et al., "EULAR/ERA-EDTA recommendations for the management of ANCA-associated vasculitis," Ann Rheum Dis 2016;75:1583-1594.
Bondebjerg, J. et al., "Novel semicarbazide-derived inhibitors of human dipeptidyl peptidase I (hDPPI)," Bioorg Med Chem. 2005;13:4408-4424.
Bondejberg, J. et al., "Dipeptidyl Nitriles as Human Dipeptidyl Peptidase 1 Inhibitors," Bioorg Med Chem Lett. 2006;16:3614-3617.
Chalmers, J. D. et al., "Phase 2 Trial of the DPP-1 Inhibitor Brensocatib in Bronchiectasis," N Engl J Med. Nov. 26, 2020;383(22):2127-2137. doi: 10.1056/NEJMoa2021713.
Chalmers, J. D. et al., "Neutrophil Elastase Activity Is Associated with Exacerbations and Lung Function Decline in Bronchiectasis," Am J Respir Crit Care Med. 2017; 195(10):1384-1393.
Gardiner, P. et al., "Neutrophil maturation rate determines the effects of dipeptidyl peptidase 1 inhibition on neutrophil serine protease activity," Br J Pharmacol. 2016;173:2390-401.
Guarino, C. et al., "Prolonged pharmacological inhibition of cathepsin C results in elimination of neutrophil serine proteases," Biochem Pharmacol. 2017;131:52-67.
Guay, D. et al., "Therapeutic Utility and Medicinal chemistry of Cathepsin C Inhibitors," Curr Top Med Chem. 2010;10:708-716.
Guay, D. et al., "Design and synthesis of dipeptidyl nitriles as potent, selective, and reversible inhibitors of cathepsin C," Bioorg Med Chem Lett. 2009;19:5392-5396.
Korkmaz, B. et al., "Therapeutic targeting of cathepsin C: from pathophysiology to treatment," Pharmacol Ther. 2018;190:202-236.
Korkmaz, B. et al., "Lung Protection by Cathepsin C Inhibition: A New Hope for COVID-19 and ARDS?" J Med Chem. 2020;63:13258-13265. doi:10.1021/acs.jmedchem.0c00776.
Korkmaz, B. et al., "Structure-based design and in vivo anti-arthritic activity evaluation of a potent dipeptidyl cyclopropyl nitrile inhibitor of cathepsin C," Biochem Pharmacol. 2019;164:349-367.
Laine, D. I. et al., "Inhibitors of Cathepsin C (DPPI)," Expert Rev. Ther Pat. 2010;20: 497-506.
Laine, D. I. et al., "Discovery of novel cyanamide-based inhibitors of cathepsin C," ACS Med Chem Lett. 2010;2(2):142-147.
McShane, P. J. et al., "Non-cystic fibrosis bronchiectasis," Am J Respir Crit Care Med. 2013;188(6):647-656. doi: 10.1164/rccm. 201303-0411CI.
Méthot, N. et al., "Inhibition of the activation of multiple serine proteases with a cathepsin C inhibitor requires sustained exposure to prevent proenzyme processing," J. Biol Chem. 2007;282:20836-20846.
Méthot, N. et al., "In Vivo Inhibition of Serine Proteases\ Processing Requires a High Fractional Inhibition of Cathepsin C," Mol. Pharm. 2008;73(6):1857-1865.
Miller, B. E. et al., "Epithelial desquamation observed in a Phase I study of an oral cathepsin C inhibitor (GSK2793660)," Br J Clin Pharmacol. 2017;83(12):2813-2820. doi: 10.1111/bcp.13398.
Palmér, R. et al., "Dipeptidyl Peptidase 1 Inhibitor AZD7986 Induces a Sustained, Exposure-Dependent Reduction in Neutrophil Elastase Activity in Healthy Subjects," Clin Pharmacol Ther. 2018;104(6):1155-1164. doi:10.1002/cpt.1053.
Pham, C. T., "Neutrophil serine proteases: specific regulators of inflammation," Nat. Rev. Immunol. Jul. 2006;6:541-550.
Rehm, S. R. T. et al., "Premedication with a cathepsin C inhibitor alleviates early primary graft dysfunction in mouse recipients after lung transplantation," Sci Rep. 2019;9(1):9925-9933.
Zhang, J. et al., "The Reversible Dipeptidyl Peptidase 1 Inhibitor, INS1007, Decreases Surface Proteinase 3 Expression and Neutrophil Serine Protease Activities in Human Neutrophils," Rheumatology. 2019;58(Supplement 2), p. ii24.
Zhang, J. et al., "INS1007, a Reversible Dipeptidyl Peptidase 1 Inhibitor, Ameliorates Interferon-alpha-Accelerated Lupus Nephritis in Mice," Abstract Review, 17th International Congress of Immunology. 2019. Abstract: A-1059-0027-00953, 1 page.
Li, J et al. (2014), "Lubricants in Pharmaceutical Solid Dosage Forms," Lubricants, 2:21-43.
Ludvigsson, J. W. et al. (2018), "Degradation caused by incompatibility between sodium stearyl fumarate (PRUV) and AZD7986 in the drug product," Journal of Pharmaceutical and Biomedical Analysis, 158:82-87.
Wang, J. et al. (2010), "Lubrication in tablet formulations," European Journal of Pharmaceutics and Biopharmaceutics, 75:1-15.
Canonica, G. W et al. (May 2020), "Chronic rhinosinusitis with nasal polyps impact in severe asthma patients: Evidences from the Severe Asthma Network Italy (SANI) registry," Respiratory Medicine, vol. 166, 105947, pp. 1-5.
Clinical Trials Identifier: NCT03218917, ClinicalTrials.gov submitted on Aug. 15, 2017, 5 pages.
Clinical Trials Identifier: NCT03218917, ClinicalTrials.gov submitted on Aug. 20, 2018, 17 pages.

(56) References Cited

OTHER PUBLICATIONS

Clinical Trials Identifier: NCT03218917, ClinicalTrials.gov submitted on Dec. 11, 2020, 10 pages.
Clinical Trials Identifier: NCT03218917, ClinicalTrials.gov submitted on Dec. 17, 2018, 17 pages.
Clinical Trials Identifier: NCT03218917, ClinicalTrials.gov submitted on Dec. 17, 2019, 10 pages.
Clinical Trials Identifier: NCT03218917, ClinicalTrials.gov submitted on Dec. 4, 2019, 10 pages.
Clinical Trials Identifier: NCT03218917, ClinicalTrials.gov submitted on Dec. 8, 2018, 17 pages.
Clinical Trials Identifier: NCT03218917, ClinicalTrials.gov submitted on Feb. 11, 2019, 17 pages.
Clinical Trials Identifier: NCT03218917, ClinicalTrials.gov submitted on Feb. 12, 2019, 17 pages.
Clinical Trials Identifier: NCT03218917, ClinicalTrials.gov submitted on Feb. 5, 2018, 5 pages.
Clinical Trials Identifier: NCT03218917, ClinicalTrials.gov submitted on Jan. 14, 2019, 17 pages.
Clinical Trials Identifier: NCT03218917, ClinicalTrials.gov submitted on Jan. 28, 2019, 17 pages.
Clinical Trials Identifier: NCT03218917, ClinicalTrials.gov submitted on Jan. 3, 2019, 17 pages.
Clinical Trials Identifier: NCT03218917, ClinicalTrials.gov submitted on Jan. 31, 2019, 17 pages.
Clinical Trials Identifier: NCT03218917, ClinicalTrials.gov submitted on Jul. 12, 2017, 7 pages.
Clinical Trials Identifier: NCT03218917, ClinicalTrials.gov submitted on Jul. 30, 2018, 5 pages.
Clinical Trials Identifier: NCT03218917, ClinicalTrials.gov submitted on Mar. 28, 2019, 16 pages.
Clinical Trials Identifier: NCT03218917, ClinicalTrials.gov submitted on May 28, 2019, 10 pages.
Clinical Trials Identifier: NCT03218917, ClinicalTrials.gov submitted on Nov. 13, 2018, 17 pages.
Clinical Trials Identifier: NCT03218917, ClinicalTrials.gov submitted on Nov. 28, 2018, 17 pages.
Clinical Trials Identifier: NCT03218917, ClinicalTrials.gov submitted on Nov. 6, 2018, 17 pages.
Clinical Trials Identifier: NCT03218917, ClinicalTrials.gov submitted on Oct. 16, 2018, 17 pages.
Clinical Trials Identifier: NCT03218917, ClinicalTrials.gov submitted on Sep. 12, 2018, 17 pages.
Clinical Trials Identifier: NCT03218917, ClinicalTrials.gov submitted on Sep. 24, 2018, 17 pages.
Clinical Trials Identifier: NCT04594369. ClinicalTrials.gov submitted on Apr. 12, 2022, 33 pages.
Clinical Trials Identifier: NCT04594369. ClinicalTrials.gov submitted on Apr. 22, 2021, 14 pages.
Clinical Trials Identifier: NCT04594369. ClinicalTrials.gov submitted on Apr. 22, 2022, 32 pages.
Clinical Trials Identifier: NCT04594369. ClinicalTrials.gov submitted on Apr. 5, 2022, 32 pages.
Clinical Trials Identifier: NCT04594369. ClinicalTrials.gov submitted on Apr. 9, 2021, 13 pages.
Clinical Trials Identifier: NCT04594369. ClinicalTrials.gov submitted on Aug. 1, 2022, 32 pages.
Clinical Trials Identifier: NCT04594369. ClinicalTrials.gov submitted on Aug. 18, 2022, 32 pages.
Clinical Trials Identifier: NCT04594369. ClinicalTrials.gov submitted on Aug. 23, 2021, 24 pages.
Clinical Trials Identifier: NCT04594369. ClinicalTrials.gov submitted on Aug. 30, 2022, 32 pages.
Clinical Trials Identifier: NCT04594369. ClinicalTrials.gov submitted on Aug. 9, 2021, 23 pages.
Clinical Trials Identifier: NCT04594369. ClinicalTrials.gov submitted on Dec. 1, 2020, 6 pages.
Clinical Trials Identifier: NCT04594369. ClinicalTrials.gov submitted on Dec. 10, 2020, 6 pages.
Clinical Trials Identifier: NCT04594369. ClinicalTrials.gov submitted on Dec. 3, 2021, 28 pages.
Clinical Trials Identifier: NCT04594369. ClinicalTrials.gov submitted on Jul. 11, 2022, 32 pages.
Clinical Trials Identifier: NCT04594369. ClinicalTrials.gov submitted on Jul. 23, 2021, 21 pages.
Clinical Trials Identifier: NCT04594369. ClinicalTrials.gov submitted on Jul. 27, 2022, 32 pages.
Clinical Trials Identifier: NCT04594369. ClinicalTrials.gov submitted on Jul. 9, 2021, 21 pages.
Clinical Trials Identifier: NCT04594369. ClinicalTrials.gov submitted on Jun. 20, 2022, 32 pages.
Clinical Trials Identifier: NCT04594369. ClinicalTrials.gov submitted on Jun. 21, 2021, 19 pages.
Clinical Trials Identifier: NCT04594369. ClinicalTrials.gov submitted on Jun. 24, 2021, 19 pages.
Clinical Trials Identifier: NCT04594369. ClinicalTrials.gov submitted on Jun. 30, 2021, 20 pages.
Clinical Trials Identifier: NCT04594369. ClinicalTrials.gov submitted on Jun. 7, 2021, 19 pages.
Clinical Trials Identifier: NCT04594369. ClinicalTrials.gov submitted on Jun. 7, 2022, 32 pages.
Clinical Trials Identifier: NCT04594369. ClinicalTrials.gov submitted on Mar. 11, 2021, 9 pages.
Clinical Trials Identifier: NCT04594369. ClinicalTrials.gov submitted on Mar. 25, 2021, 11 pages.
Clinical Trials Identifier: NCT04594369. ClinicalTrials.gov submitted on Mar. 25, 2022, 34 pages.
Clinical Trials Identifier: NCT04594369. ClinicalTrials.gov submitted on Mar. 4, 2022, 32 pages.
Clinical Trials Identifier: NCT04594369. ClinicalTrials.gov submitted on May 13, 2022, 33 pages.
Clinical Trials Identifier: NCT04594369. ClinicalTrials.gov submitted on May 25, 2022, 31 pages.
Clinical Trials Identifier: NCT04594369. ClinicalTrials.gov submitted on Nov. 10, 2021, 29 pages.
Clinical Trials Identifier: NCT04594369. ClinicalTrials.gov submitted on Nov. 15, 2022, 30 pages.
Clinical Trials Identifier: NCT04594369. ClinicalTrials.gov submitted on Nov. 19, 2020, 6 pages.
Clinical Trials Identifier: NCT04594369. ClinicalTrials.gov submitted on Nov. 23, 2022, 30 pages.
Clinical Trials Identifier: NCT04594369. ClinicalTrials.gov submitted on Oct. 10, 2022, 31 pages.
Clinical Trials Identifier: NCT04594369. ClinicalTrials.gov submitted on Oct. 14, 2020, 6 pages.
Clinical Trials Identifier: NCT04594369. ClinicalTrials.gov submitted on Oct. 27, 2022, 31 pages.
Clinical Trials Identifier: NCT04594369. ClinicalTrials.gov submitted on Oct. 28, 2021, 29 pages.
Clinical Trials Identifier: NCT04594369. ClinicalTrials.gov submitted on Oct. 29, 2021, 29 pages.
Clinical Trials Identifier: NCT04594369. ClinicalTrials.gov submitted on Oct. 8, 2021, 28 pages.
Clinical Trials Identifier: NCT04594369. ClinicalTrials.gov submitted on Sep. 12, 2022, 31 pages.
Clinical Trials Identifier: NCT04594369. ClinicalTrials.gov submitted on Sep. 27, 2022, 31 pages.
Clinical Trials Identifier: NCT04594369. ClinicalTrials.gov submitted on Sep. 7, 2021, 25 pages.
Clinical Trials Identifier: NCT04817332. ClinicalTrials.gov submitted on Aug. 12, 2021, 8 pages.
Clinical Trials Identifier: NCT04817332. ClinicalTrials.gov submitted on Mar. 25, 2021, 8 pages.
Clinical Trials Identifier: NCT05090904. ClinicalTrials.gov submitted on Apr. 14, 2022, 6 pages.
Clinical Trials Identifier: NCT05090904. ClinicalTrials.gov submitted on Apr. 5, 2022, 6 pages.
Clinical Trials Identifier: NCT05090904. ClinicalTrials.gov submitted on Aug. 23, 2022, 7 pages.
Clinical Trials Identifier: NCT05090904. ClinicalTrials.gov submitted on Dec. 3, 2021, 6 pages.

(56) References Cited

OTHER PUBLICATIONS

Clinical Trials Identifier: NCT05090904. ClinicalTrials.gov submitted on Jul. 27, 2022, 7 pages.
Clinical Trials Identifier: NCT05090904. ClinicalTrials.gov submitted on Jul. 29, 2022, 7 pages.
Clinical Trials Identifier: NCT05090904. ClinicalTrials.gov submitted on Jul. 4, 2022, 7 pages.
Clinical Trials Identifier: NCT05090904. ClinicalTrials.gov submitted on Jun. 22, 2022, 7 pages.
Clinical Trials Identifier: NCT05090904. ClinicalTrials.gov submitted on Jun. 7, 2022, 7 pages.
Clinical Trials Identifier: NCT05090904. ClinicalTrials.gov submitted on Mar. 8, 2022, 6 pages.
Clinical Trials Identifier: NCT05090904. ClinicalTrials.gov submitted on May 13, 2022, 7 pages.
Clinical Trials Identifier: NCT05090904. ClinicalTrials.gov submitted on May 25, 2022, 7 pages.
Clinical Trials Identifier: NCT05090904. ClinicalTrials.gov submitted on Nov. 10, 2022, 7 pages.
Clinical Trials Identifier: NCT05090904. ClinicalTrials.gov submitted on Oct. 12, 2022, 7 pages.
Clinical Trials Identifier: NCT05090904. ClinicalTrials.gov submitted on Oct. 14, 2021, 5 pages.
Clinical Trials Identifier: NCT05090904. ClinicalTrials.gov submitted on Oct. 29, 2021, 5 pages.
Clinical Trials Identifier: NCT05090904. ClinicalTrials.gov submitted on Sep. 9, 2022, 7 pages.
Clinical Trials Identifier: NCT05344508. ClinicalTrials.gov submitted on Apr. 18, 2022, 3 pages.
Clinical Trials Identifier: NCT05344508. ClinicalTrials.gov submitted on Aug. 3, 2022, 3 pages.
Clinical Trials Identifier: NCT05344508. ClinicalTrials.gov submitted on Oct. 6, 2022, 3 pages.
Clinical Trials Identifier: NCT05355935. ClinicalTrials.gov submitted on Apr. 26, 2022, 6 pages.
Clinical Trials Identifier: NCT05355935. ClinicalTrials.gov submitted on Aug. 16, 2022, 6 pages.
Clinical Trials Identifier: NCT05355935. ClinicalTrials.gov submitted on Jul. 27, 2022, 6 pages.
Clinical Trials Identifier: NCT05355935. ClinicalTrials.gov submitted on Jul. 5, 2022, 6 pages.
Clinical Trials Identifier: NCT05355935. ClinicalTrials.gov submitted on Jun. 7, 2022, 6 pages.
Clinical Trials Identifier: NCT05355935. ClinicalTrials.gov submitted on May 16, 2022, 6 pages.
Clinical Trials Identifier: NCT05355935. ClinicalTrials.gov submitted on Oct. 19, 2022, 5 pages.
Clinical Trials Identifier: NCT05355935. ClinicalTrials.gov submitted on Sep. 9, 2022, 6 pages.
Clinical Trials Identifier: NCT05517525. ClinicalTrials.gov submitted on Aug. 24, 2022, 5 pages.
Clinical Trials Identifier: NCT05517525. ClinicalTrials.gov submitted on Nov. 7, 2022, 4 pages.
Clinical Trials Identifier: NCT05517525. ClinicalTrials.gov submitted on Oct. 17, 2022, 4 pages.
Clinical Trials Identifier: NCT05517525. ClinicalTrials.gov submitted on Sep. 21, 2022, 5 pages.
Gerald, L. B. et al. (Apr. 2009), "Changes in environmental tobacco smoke exposure and asthma morbidity among urban school children," Chest, vol. 135, No. 4, pp. 911-916.
Insmed Announces Worldwide License Agreement with AstraZeneca for Oral DPP1 Inhibitor, Oct. 2016, 3 pages.
International Preliminary Report on Patentability for International Application No. PCT/US2021/064810, dated Jul. 6, 2023, 6 pages.
International Preliminary Report on Patentability for International Application No. PCT/US2022/027026, dated Nov. 9, 2023, 8 pages.
International Search Report and Written Opinion for International Application No. PCT/US2022/048249, mailed Feb. 1, 2023, 8 pages.
International Search Report and Written Opinion for International Application No. PCT/US2023/062731, dated May 30, 2023, 32 pages.
Korkmaz, B. et al., "Cathepsin C inhibition as a potential treatment strategy in cancer," Biochemical Pharmacology, 194 (Dec. 2021): 114803, 15 pages.
Rosati, M. G. et al. (Jan.-Feb. 2016), "Relationships among allergic rhinitis, asthma, and chronic rhinosinusitis," American Journal of Rhinology and Allergy, vol. 30, No. 1, pp. 44-47.

CERTAIN (2S)-N-[(1S)-1-CYANO-2-PHENYLETHYL]-1,4-OXAZEPANE-2-CARBOXAMIDES FOR TREATING LUPUS NEPHRITIS

CROSS REFERENCE TO RELATED APPLICATION

This is a U.S. National Phase application of PCT/US2019/042021, filed Jul. 16, 2019, which claims priority from U.S. Provisional Application Ser. No. 62/699,494, filed Jul. 17, 2018, the disclosures of which are incorporated by reference herein in their entireties for all purposes.

BACKGROUND OF THE INVENTION

Lupus nephritis (LN) is an autoimmune-mediated glomuleronephritis that is one of the most common and serious manifestations of systemic lupus erythematosus (SLE). Ward (2014). Rheum. Dis. Clin. North Am. 40(3), pp. 519-535. Currently, there are no curative treatments for LN.

Treatment options for LN include powerful immunosuppressive drugs such as high-dose corticosteroids, e.g., glucocorticoids, alone or in combination with cytotoxic drugs.

There is still a need for new LN treatments with less toxicity and better efficacy. The present invention addresses this and other needs.

SUMMARY OF THE INVENTION

In one aspect, a method is provided for treating a lupus nephritis (LN) patient in need thereof. The method comprises, in one embodiment, administering to the LN patient in need of treatment, a pharmaceutical composition comprising an effective amount of a compound of formula (I), or a pharmaceutically acceptable salt thereof.

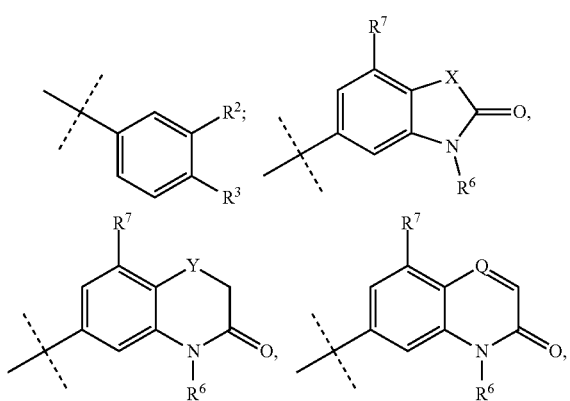

(I)

wherein,
$R^1$ is

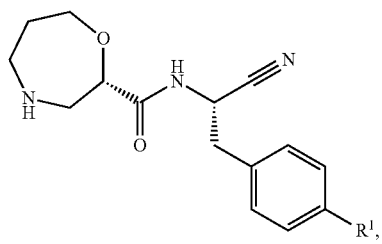

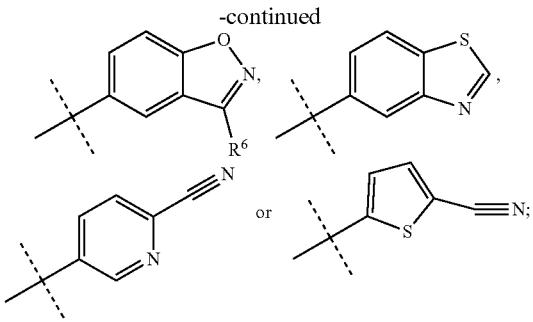

$R^2$ is hydrogen, F, Cl, Br, $OSO_2C_{1-3}$alkyl, or $C_{1-3}$alkyl;

$R^3$ is hydrogen, F, Cl, Br, CN, $CF_3$, $SO_2C_{1-3}$alkyl, $CONH_2$ or $SO_2NR^4R^5$, wherein $R^4$ and $R^5$ together with the nitrogen atom to which they are attached form an azetidine, pyrrolidine or piperidine ring; or $R^6$ is $C_{1-3}$alkyl, optionally substituted by 1, 2 or 3 F and/or optionally by OH, $OC_{1-3}$alkyl, $N(C_{1-3}alkyl)_2$, cyclopropyl, or tetrahydropyran;

$R^7$ is hydrogen, F, Cl or $CH_3$;

X is O, S or $CF_2$;

Y is O or S; and

Q is CH or N.

In one embodiment of the method for treating LN in a patient in need thereof, the pharmaceutical composition comprises an effective amount of (2S)—N-{(1S)-1-cyano-2-[4-(3-methyl-2-oxo-2,3-dihydro-1,3-benzoxazol-5-yl)phenyl]ethyl}-1,4-oxazepane-2-carboxamide, (also referred to herein as INS1007),

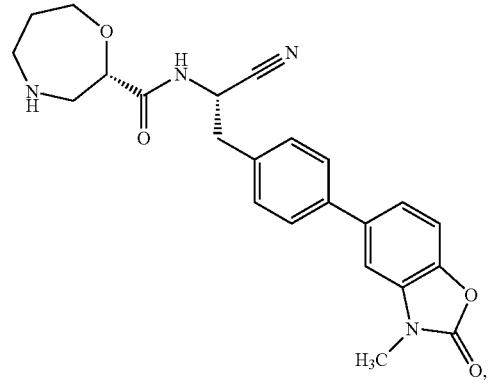

or a pharmaceutically acceptable salt thereof.

Administration routes include oral administration. Administration schedules can be determined by the user of the method, e.g., a prescribing physician. In one embodiment, administration is once daily. In another embodiment, administration is twice daily. In another embodiment, administration 1× daily, once every other day, once every third day, once every fourth day, 2× weekly, 3× weekly or 4× weekly.

DETAILED DESCRIPTION OF THE INVENTION

Figure 1:
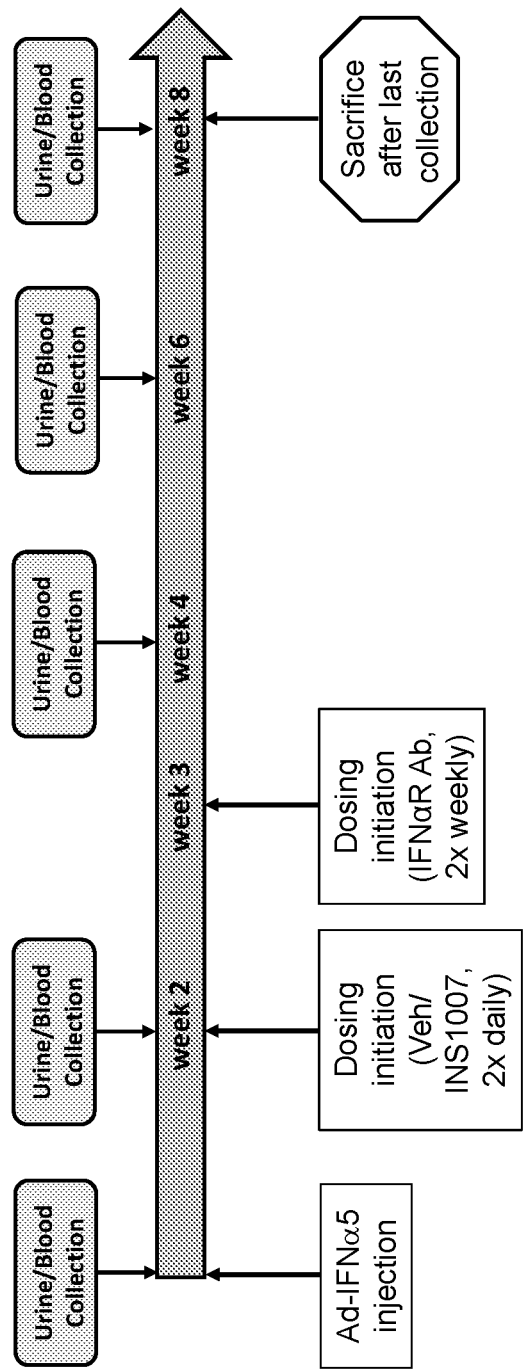
FIG. 1 is a schematic of the accelerated LN model and study design described in Example 2.

The methods provided herein employ reversible inhibitors of DPP1 in methods for treating LN.

As used herein, "$C_{1-3}$" means a carbon group having 1, 2 or 3 carbon atoms.

The term "alkyl", unless otherwise noted, includes both straight and branched chain alkyl groups and may be substituted or non-substituted. "Alkyl" groups include, but are not limited to, methyl, ethyl, n-propyl, i-propyl, butyl, pentyl.

The term "pharmaceutically acceptable", unless otherwise noted, is used to characterize a moiety (e.g., a salt, dosage form, or excipient) as being appropriate for use in accordance with sound medical judgment. In general, a pharmaceutically acceptable moiety has one or more benefits that outweigh any deleterious effect that the moiety may have. Deleterious effects may include, for example, excessive toxicity, irritation, allergic response, and other problems and complications.

Provided herein are methods for treating LN patients via administration of a pharmaceutical composition comprising an effective amount of a compound of formula (I), or a pharmaceutically acceptable salt thereof:

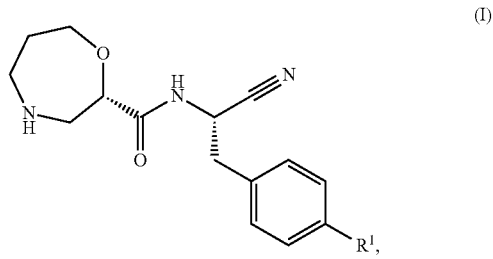

(I)

wherein,

R is

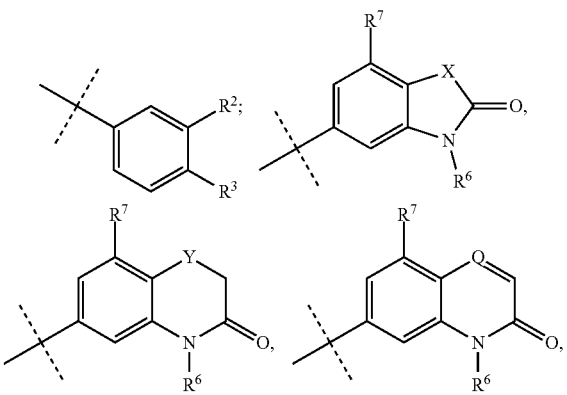

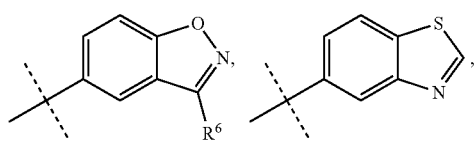

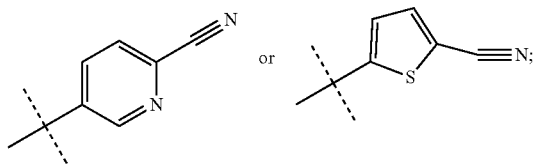

$R^2$ is hydrogen, F, Cl, Br, $OSO_2C_{1-3}$alkyl, or $C_{1-3}$alkyl;

$R^3$ is hydrogen, F, Cl, Br, CN, $CF_3$, $SO_2C_{1-3}$alkyl, $CONH_2$ or $SO_2NR^4R^5$, wherein $R^4$ and $R^5$ together with the nitrogen atom to which they are attached form an azetidine, pyrrolidine or piperidine ring; or $R^6$ is $C_{1-3}$alkyl, optionally substituted by 1, 2 or 3 F and/or optionally by OH, $OC_{1-3}$alkyl, $N(C_{1-3}alkyl)_2$, cyclopropyl, or tetrahydropyran;

$R^7$ is hydrogen, F, Cl or $CH_3$;

X is O, S or $CF_2$;

Y is O or S; and

Q is CH or N.

In one embodiment $R^1$ is

[structure: phenyl with $R^2$ and $R^3$ substituents]

$R^2$ is hydrogen, F, Cl, Br, $OSO_2C_{1-3}$alkyl, or $C_{1-3}$alkyl; $R^3$ is hydrogen, F, Cl, Br, CN, $CF_3$, $SO_2C_{1-3}$alkyl, $CONH_2$ or $SO_2NR^4R^5$, wherein $R^4$ and $R^5$ together with the nitrogen atom to which they are attached form an azetidine, pyrrolidine or piperidine ring.

In a further embodiment, $R^1$ is

[structure: phenyl with $R^2$ and $R^3$ substituents]

$R^2$ is hydrogen, F, Cl or $C_{1-3}$alkyl; and $R^3$ is hydrogen, F, Cl, CN or $SO_2C_{1-3}$alkyl.

In still a further embodiment, $R^1$ is

[structure: phenyl with $R^2$ and $R^3$ substituents]

$R^2$ is hydrogen, F or $C_{1-3}$alkyl; and $R^3$ is hydrogen, F or CN.

In another embodiment, $R^1$ is

[structures: benzoxazolone-type with X, $R^6$, $R^7$; benzoxazine-type with Y, $R^6$, $R^7$; benzoxazinone; benzisoxazole with $R^6$; benzothiazole; pyridine-CN]

or

[structure: thiophene with CN]

X is O, S or $CF_2$; Y is O or S; Q is CH or N; $R^6$ is $C_{1-3}$alkyl, wherein the $C_{1-3}$alkyl is optionally substituted by 1, 2 or 3 F and/or optionally substituted by OH, $OC_{1-3}$alkyl, $N(C_{1-3}$alkyl$)_2$, cyclopropyl, or tetrahydropyran; and $R^7$ is hydrogen, F, Cl or $CH_3$.

In still a further embodiment, $R^1$ is

[structure: benzoxazolone with X, $R^6$, $R^7$] or

[structure: benzoxazine with Y, $R^6$, $R^7$]

X is O, S or $CF_2$; Y is O or S; $R^6$ is $C_{1-3}$alkyl, optionally substituted by 1, 2 or 3 F and optionally substituted by OH, $OC_{1-3}$alkyl, $N(C_{1-3}$alkyl$)_2$, cyclopropyl, or tetrahydropyran; and $R^7$ is hydrogen, F, Cl or $CH_3$.

In still a further embodiment, $R^1$ is

[structure: benzoxazolone with X, $R^6$, $R^7$]

X is O, S or $CF_2$; $R^6$ is $C_{1-3}$alkyl, wherein the $C_{1-3}$alkyl is optionally substituted by 1, 2 or 3 F; and $R^7$ is hydrogen, F, Cl or $CH_3$.

In still a further embodiment, $R^1$ is

[structure: benzoxazolone with X, $R^6$, $R^7$]

X is O; $R^6$ is $C_{1-3}$alkyl, wherein the $C_{1-3}$alkyl is optionally substituted by 1, 2 or 3 F; and $R^7$ is hydrogen.

In one embodiment, $R^2$ is hydrogen, F, Cl, Br, $OSO_2C_{1-3}$alkyl or $C_{1-3}$alkyl.

In a further embodiment, $R^2$ is hydrogen, F, Cl or $C_{1-3}$alkyl.

In still a further embodiment, $R^2$ is hydrogen, F or $C_{1-3}$alkyl.

In one embodiment, $R^3$ is hydrogen, F, Cl, Br, CN, $CF_3$, $SO_2C_{1-3}$alkyl $CONH_2$ or $SO_2NR^4R^5$, wherein $R^4$ and $R^5$ together with the nitrogen atom to which they are attached form an azetidine, pyrrolidine or piperidine ring.

In a further embodiment, $R^3$ is selected from hydrogen, F, Cl, CN or $SO_2C_{1-3}$alkyl.

In still a further embodiment, $R^3$ is selected from hydrogen, F or CN.

In one embodiment, $R^6$ is $C_{1-3}$alkyl, wherein said $C_{1-3}$alkyl is optionally substituted by 1, 2 or 3 F and optionally by one substituent selected from OH, $OC_{1-3}$alkyl, $N(C_{1-3}$alkyl$)_2$, cyclopropyl, or tetrahydropyran.

In a further embodiment, $R^6$ is $C_{1-3}$alkyl, wherein said $C_{1-3}$alkyl is optionally substituted by 1, 2 or 3 F. In still a further embodiment, $R^6$ is methyl or ethyl. In still a further embodiment, $R^6$ is methyl.

In one embodiment, $R^7$ is hydrogen, F, Cl or $CH_3$. In a further embodiment, $R^7$ is hydrogen.

In one embodiment of the methods provided herein, the composition administered to the patient comprises an effective amount of (2S)—N-{(1S)-1-cyano-2-[4-(3-methyl-2-oxo-2,3-dihydro-1,3-benzoxazol-5-yl)phenyl]ethyl}-1,4-oxazepane-2-carboxamide (INS1007):

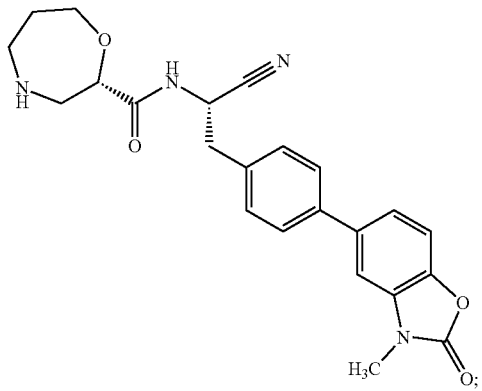 [SMILES: Cn1c(=O)oc2ccc(-c3ccc(C[C@@H](C#N)NC(=O)[C@@H]4CNCCCO4)cc3)cc21]

or a pharmaceutically acceptable salt thereof.

In one embodiment, the compound of formula (I) is:
(2S)—N-[(1S)-1-Cyano-2-(4'-cyanobiphenyl-4-yl)ethyl]-1,4-oxazepane-2-carboxamide,
(2S)—N-{(1S)-1-Cyano-2-[4-(3-methyl-2-oxo-2,3-dihydro-1,3-benzoxazol-5-yl)phenyl]ethyl}-1,4-oxazepane-2-carboxamide,
(2S)—N-{(1S)-1-Cyano-2-[4-(3,7-dimethyl-2-oxo-2,3-dihydro-1,3-benzoxazol-5-yl)phenyl]ethyl}-1,4-oxazepane-2-carboxamide,
4'-[(2S)-2-Cyano-2-{[(2S)-1,4-oxazepan-2-ylcarbonyl]amino}ethyl]biphenyl-3-yl methanesulfonate,
(2S)—N-{(1S)-1-Cyano-2-[4-(3-methyl-1,2-benzoxazol-5-yl)phenyl]ethyl}-1,4-oxazepane-2-carboxamide,
(2S)—N-{(1S)-1-Cyano-2-[4'-(trifluoromethyl)biphenyl-4-yl]ethyl}-1,4-oxazepane-2-carboxamide,
(2S)—N-[(1S)-1-Cyano-2-(3',4'-difluorobiphenyl-4-yl)ethyl]-1,4-oxazepane-2-carboxamide,
(2S)—N-{(1S)-1-Cyano-2-[4-(6-cyanopyridin-3-yl)phenyl]ethyl}-1,4-oxazepane-2-carboxamide,
(2S)—N-{(1S)-1-Cyano-2-[4-(4-methyl-3-oxo-3,4-dihydro-2H-1,4-benzothiazin-6-yl)phenyl]ethyl}-1,4-oxazepane-2-carboxamide,
(2S)—N-{(1S)-1-Cyano-2-[4-(3-ethyl-7-methyl-2-oxo-2,3-dihydro-1,3-benzoxazol-5-yl)phenyl]ethyl}-1,4-oxazepane-2-carboxamide,
(2S)—N-[(1S)-1-Cyano-2-{4-[3-(2-hydroxy-2-methylpropyl)-2-oxo-2,3-dihydro-1,3-benzoxazol-5-yl]phenyl}ethyl]-1,4-oxazepane-2-carboxamide,
(2S)—N-[(1S)-1-Cyano-2-{4-[3-(2,2-difluoroethyl)-7-fluoro-2-oxo-2,3-dihydro-1,3-benzoxazol-5-yl]phenyl}ethyl]-1,4-oxazepane-2-carboxamide,
(2S)—N-[(1S)-1-Cyano-2-(4-{3-[2-(dimethylamino)ethyl]-2-oxo-2,3-dihydro-1,3-benzoxazol-5-yl}phenyl)ethyl]-1,4-oxazepane-2-carboxamide,
(2S)—N-{(1S)-1-Cyano-2-[4-(3,3-difluoro-1-methyl-2-oxo-2,3-dihydro-1H-indol-6-yl)phenyl]ethyl}-1,4-oxazepane-2-carboxamide,
(2S)—N-{(1S)-1-Cyano-2-[4-(7-fluoro-3-methyl-2-oxo-2,3-dihydro-1,3-benzoxazol-5-yl)phenyl]ethyl}-1,4-oxazepane-2-carboxamide,
(2S)—N-{(1S)-1-Cyano-2-[4-(3-ethyl-2-oxo-2,3-dihydro-1,3-benzoxazol-5-yl)phenyl]ethyl}-1,4-oxazepane-2-carboxamide,
(2S)—N-[(1S)-1-Cyano-2-{4-[3-(cyclopropylmethyl)-2-oxo-2,3-dihydro-1,3-benzoxazol-5-yl]phenyl}ethyl]-1,4-oxazepane-2-carboxamide,
(2S)—N-[(1S)-1-Cyano-2-{4-[3-(2-methoxyethyl)-2-oxo-2,3-dihydro-1,3-benzothiazol-5-yl]phenyl}ethyl]-1,4-oxazepane-2-carboxamide,
(2S)—N-[(1S)-1-Cyano-2-{4-[2-oxo-3-(propan-2-yl)-2,3-dihydro-1,3-benzoxazol-5-yl]phenyl}ethyl]-1,4-oxazepane-2-carboxamide,
(2S)—N-{(1S)-1-Cyano-2-[4-(4-methyl-3-oxo-3,4-dihydro-2H-1,4-benzoxazin-6-yl)phenyl]ethyl}-1,4-oxazepane-2-carboxamide,
(2S)—N-[(1S)-1-Cyano-2-{4-[3-(2-methoxyethyl)-2-oxo-2,3-dihydro-1,3-benzoxazol-5-yl]phenyl}ethyl]-1,4-oxazepane-2-carboxamide,
(2S)—N-{(1S)-1-Cyano-2-[4-(5-cyanothiophen-2-yl)phenyl]ethyl}-1,4-oxazepane-2-carboxamide,
(2S)—N-[(1S)-2-(4'-Carbamoyl-3'-fluorobiphenyl-4-yl)-1-cyanoethyl]-1,4-oxazepane-2-carboxamide,
(2S)—N-{(1S)-1-Cyano-2-[4-(1-methyl-2-oxo-1,2-dihydroquinolin-7-yl)phenyl]ethyl}-1,4-oxazepane-2-carboxamide,
(2S)—N-[(1S)-1-Cyano-2-{4-[2-oxo-3-(tetrahydro-2H-pyran-4-ylmethyl)-2,3-dihydro-1,3-benzoxazol-5-yl]phenyl}ethyl]-1,4-oxazepane-2-carboxamide,
(2S)—N-{(1S)-2-[4-(7-Chloro-3-methyl-2-oxo-2,3-dihydro-1,3-benzoxazol-5-yl)phenyl]-1-cyanoethyl}-1,4-oxazepane-2-carboxamide,
(2S)—N-[(1S)-1-Cyano-2-{4-[3-(2,2-difluoroethyl)-2-oxo-2,3-dihydro-1,3-benzoxazol-5-yl]phenyl}ethyl]-1,4-oxazepane-2-carboxamide,
(2S)—N-[(1S)-1-Cyano-2-{4-[2-oxo-3-(2,2,2-trifluoroethyl)-2,3-dihydro-1,3-benzoxazol-5-yl]phenyl}ethyl]-1,4-oxazepane-2-carboxamide,
(2S)—N-{(1S)-1-Cyano-2-[4-(3-methyl-2-oxo-2,3-dihydro-1,3-benzothiazol-5-yl)phenyl]ethyl}-1,4-oxazepane-2-carboxamide,
(2S)—N-{(1S)-1-Cyano-2-[4'-(methylsulfonyl)biphenyl-4-yl]ethyl}-1,4-oxazepane-2-carboxamide,
(2S)—N-{(1S)-2-[4'-(Azetidin-1-ylsulfonyl)biphenyl-4-yl]-1-cyanoethyl}-1,4-oxazepane-2-carboxamide,
(2S)—N-[(1S)-1-Cyano-2-(4'-fluorobiphenyl-4-yl)ethyl]-1,4-oxazepane-2-carboxamide,
(2S)—N-{(1S)-2-[4-(1,3-Benzothiazol-5-yl)phenyl]-1-cyanoethyl}-1,4-oxazepane-2-carboxamide, or (2S)—N-[(1S)-1-Cyano-2-(4'-cyanobiphenyl-4-yl)ethyl]-1,4-oxazepane-2-carboxamide,
or a pharmaceutically acceptable salt of one of the foregoing compounds.

Formula I, its subgenuses, and specific compounds of Formula (I), including INS1007, as well as methods of making the same, are disclosed in U.S. Pat. No. 9,522,894, the disclosure of which is incorporated by reference in its entirety for all purposes.

The LN treatment methods provided herein comprise the administration of a composition comprising an effective amount of a compound of formula (I), or a pharmaceutically acceptable salt thereof, to a patient in need of LN treatment. The compounds of formula (I) and their pharmaceutically acceptable salts are inhibitors of dipeptidyl peptidase 1 (DPP1) activity. In one embodiment, the compound is INS1007, or a pharmaceutically acceptable salt thereof.

Administration routes include oral administration. Administration schedules can be determined by the user of the method, e.g., a prescribing physician. In one embodiment, administration is once daily. In another embodiment, administration is twice daily. In another embodiment, administration 1× daily, once every other day, once every third day, once every fourth day, 2× weekly, 3× weekly or 4× weekly. In one embodiment, the patient is administered a compound of formula (I) 1× daily at a dosage of 10 mg, 25 mg or 40 mg.

The term "treating" in one embodiment, includes: (1) preventing or delaying the appearance of clinical symptoms of the state, disorder or condition developing in the patient that may be afflicted with or predisposed to the state, disorder or condition but does not yet experience or display clinical or subclinical symptoms of the state, disorder or condition; (2) inhibiting the state, disorder or condition (e.g., arresting, reducing or delaying the development of the disease, or a relapse thereof in case of maintenance treatment, of at least one clinical or subclinical symptom thereof); (3) relieving the condition (for example, by causing regression of the state, disorder or condition or at least one of its clinical or subclinical symptoms).

In one embodiment, the methods provided herein comprise increasing the renal function of the patient being treated. Renal function, in one embodiment, is assessed via the measurement of one or more of the following: (i) blood urea nitrogen (BUN); (ii) serum creatinine; (iii) creatinine clearance. Factors that have been associated with worse renal outcomes include elevated titers of anti-double stranded DNA antibodies, low levels of C3 complement; increased levels of serum creatinine; decreased rates of creatinine clearance, increased proteinuria.

In one embodiment, treating a patient for LN comprises decreasing the serum creatinine levels in the patient, as compared to a baseline level measured prior to initiation of treatment. In one embodiment, decreasing the serum creatinine comprises decreasing to the normal range for serum creatinine. In one embodiment, the normal range for serum creatinine may be from about 0.6 to about 1.3 mg/dL, with some variation seen by age, between men and women, and from lab to lab.

In another embodiment, treating a patient for LN comprises decreasing the active urinary sediment and/or casts in the patient, or obtaining an inactive urinary sediment in the patient. The presence of urinary sediment and/or casts may be measured, e.g., by microscopic examination of urine. For example, the number of red blood cells in a urine sample may be assayed by microscopic examination. In some embodiments, an inactive urinary sediment is defined as less than about 10 red blood cells (RBC) per high power field (HPF). Urinary casts may include without limitation red blood cell casts, white blood cell casts, renal tubular epithelial cell casts, waxy casts, hyaline casts, granular casts, and fatty casts.

In some embodiments, a urinary protein to creatinine ratio (UPCR) may be measured and assessed for treatment efficacy. For example, treating in one embodiment comprises decreasing the UPCR in the patient, as compared to an initial value measured prior to treatment initiation.

The presence of protein in the urine (proteinuria) may also be assayed by tests including without limitation a urine albumin to creatinine ratio (UACR) and dipstick urinalysis. Treatment in one embodiment, comprises decreasing proteinuria in the patient, as compared to an initial value measured prior to treatment initiation.

Other tests and/or measures that may be useful for examining renal function include without limitation a renal panel, creatinine clearance, sodium, potassium, chloride, bicarbonate, phosphorus, calcium, albumin, blood urea nitrogen (BUN), creatinine, glucose, estimated glomerular filtration rate (eGFR), BUN/creatinine ratio, and anion gap, and may include a measurement of the above parameters in the blood and/or urine, where appropriate. For more detailed description, see, e.g., the American College of Rheumatology Guidelines for Screening, Case Definition, Treatment and Management of Lupus Nephritis (Hahn, B. et al. (2012) Arthritis Care Res. 64:797-808, incorporated by reference herein in its entirety for all purposes).

In one embodiment, treating a patient for LN comprises achieving a complete renal response (CRR) or a partial renal response (PRR) in the patient.

As used herein, "complete renal response" or "CRR" refers to a response to treatment that includes a normalization of serum creatinine, inactive urinary sediment, and a urinary protein to creatinine ratio of less than 0.5.

"Partial renal response" or "PRR" as used herein, refers to a response to treatment that is less than a CRR but still includes mitigation of one or more symptoms including without limitation a reduction in serum creatinine, reduced urinary sediment, and a reduction in proteinuria.

CRR or PRR is measured, for example, about 3 months, about 6 months, about 9 months or about 12 months after the initiation of one of the methods of treatment provided herein.

In one embodiment, CRR is defined by the following characteristics:
 (a) normalization of serum creatine as evidenced by:
  (i) serum creatinine≤to the upper limit of normal (ULN) range of central laboratory values if the baseline (Day 1) is not within the normal range of the central laboratory values; and
  (ii) serum creatinine≤15% above baseline and less than or equal to the ULN range of central laboratory values if baseline (Day 1) serum creatinine is within the normal range of the central laboratory values;
 (b) Inactive urinary sediment (as evidenced by <10 RBCs/high-power field (HPF) and the absence of red cell casts); and
 (c) Urinary protein to creatinine ratio<0.5.

In one embodiment, treating a patient for LN comprises decreasing the proteinuria in the patient, as compared to a baseline value. The baseline value is taken in one embodiment, immediately prior to initiation of one of the treatment methods provided herein.

In a further embodiment, a composition comprising an effective amount of a compound of Formula (I) is administered orally. In a further embodiment, the compound of Formula (I) is INS1007, or a pharmaceutically acceptable salt thereof. In yet a further embodiment, administration is 1× daily, once every other day, once every third day, once every fourth day, 2× weekly, 3× weekly or 4× weekly. In even a further embodiment, administration of the compound is once daily.

The dosage administered will vary with the compound employed, the mode of administration, the treatment desired and the disorder indicated. In one embodiment, if the compound is administered orally, then the daily dosage of the compound of the disclosure may be in the range from 0.01 micrograms per kilogram body weight (μg/kg) to 100 milligrams per kilogram body weight (mg/kg).

In one embodiment, the compound of Formula (I) is administered in an oral dosage form. In a further embodiment, the compound of Formula (I) is administered as a 10 mg to 50 mg dosage form, for example, a 5 mg dosage form, a 10 mg dosage form, a 15 mg dosage form, a 20 mg dosage form, a 25 mg dosage form, a 30 mg dosage form, 35 mg dosage form, a 40 mg dosage form, a 45 mg dosage form or a 50 mg dosage form. In a further embodiment, the dosage form is a 25 mg or 40 mg dosage form. In a further embodiment, the dosage form is administered once daily. In even a further embodiment, the compound is (2S)—N-{(1S)-1-cyano-2-[4-(3-methyl-2-oxo-2,3-dihydro-1,3-benzoxazol-5-yl)phenyl]ethyl}-1,4-oxazepane-2-carboxamide, or a pharmaceutically acceptable salt thereof.

Treating, in one embodiment, is carried out over an administration period of about 3 months, about 6 months, about 9 months, about 12 months, about 15 months, about 18 months, about 21 months or about 24 months.

The compounds of formula (I), or pharmaceutically acceptable salts thereof, may be used on their own but will generally be administered in the form of a pharmaceutical composition in which the formula (I) compound/salt (active ingredient) is in a composition comprising a pharmaceutically acceptable adjuvant(s), diluents(s) and/or carrier(s). Conventional procedures for the selection and preparation of suitable pharmaceutical formulations are described in, for example, "Pharmaceuticals—The Science of Dosage Form Designs", M. E. Aulton, Churchill Livingstone, $2^{nd}$ Ed. 2002, incorporated by reference herein in its entirety for all purposes.

Depending on the mode of administration, the pharmaceutical composition will comprise from 0.05 to 99% w (percent by weight), for example, from 0.05 to 80% w, or from 0.10 to 70% w, or from 0.10 to 50% w, of active ingredient, all percentages by weight being based on total composition.

In one oral administration embodiment, the oral dosage form is a film-coated oral tablet. In a further embodiment, the dosage form is an immediate release dosage form with rapid dissolution characteristics under in vitro test conditions.

In one embodiment, the oral dosage form is administered once daily. In a further embodiment, the oral dosage form is administered at approximately the same time every day, e.g., prior to breakfast. In another embodiment, the composition comprising an effective amount of formula (I) is administered 2× day. In yet another embodiment, the composition comprising an effective amount of formula (I) is administered once-a-week, every other day, every third day, 2× week, 3× week, 4× week, or 5× week.

For oral administration the compound of the disclosure may be admixed with adjuvant(s), diluent(s) or carrier(s), for example, lactose, saccharose, sorbitol, mannitol; starch, for example, potato starch, corn starch or amylopectin; cellulose derivative; binder, for example, gelatine or polyvinylpyrrolidone; disintegrant, for example cellulose derivative, and/or lubricant, for example, magnesium stearate, calcium stearate, polyethylene glycol, wax, paraffin, and the like, and then compressed into tablets. If coated tablets are required, the cores, prepared as described above, may be coated with a suitable polymer dissolved or dispersed in water or readily volatile organic solvent(s). Alternatively, the tablet may be coated with a concentrated sugar solution which may contain, for example, gum arabic, gelatine, talcum and titanium dioxide.

For the preparation of soft gelatine capsules, the compound of the disclosure may be admixed with, for example, a vegetable oil or polyethylene glycol. Hard gelatine capsules may contain granules of the compound using pharmaceutical excipients like the above-mentioned excipients for tablets. Also liquid or semisolid formulations of the compound of the disclosure may be filled into hard gelatine capsules.

In one embodiment, the composition is an oral disintegrating tablet (ODT). ODTs differ from traditional tablets in that they are designed to be dissolved on the tongue rather than swallowed whole In one embodiment, the composition is an oral thin film or an oral disintegrating film (ODF). Such formulations, when placed on the tongue, hydrate via interaction with saliva, and releases the active compound from the dosage form. The ODF, in one embodiment, contains a film-forming polymer such as hydroxypropylmethylcellulose (HPMC), hydroxypropyl cellulose (HPC), pullulan, carboxymethyl cellulose (CMC), pectin, starch, polyvinyl acetate (PVA) or sodium alginate.

Liquid preparations for oral application may be in the form of syrups, solutions or suspensions. Solutions, for example, may contain the compound of the disclosure, the balance being sugar and a mixture of ethanol, water, glycerol and propylene glycol. Optionally such liquid preparations may contain coloring agents, flavoring agents, saccharine and/or carboxymethylcellulose as a thickening agent. Furthermore, other excipients known to those skilled in art may be used when making formulations for oral use.

A compound of formula (I), or a pharmaceutically acceptable salt thereof, may also be administered in conjunction with a further compound used for the treatment of LN via one of the methods described herein.

The further compound is administered concurrently, sequentially or in admixture with a compound of Formula (I), for the treatment of LN.

In one embodiment, the further compound is an immunosuppressant. In a further embodiment, the immunosuppressant is mycophenolate mofetil (MMF) or azathioprine.

In yet another embodiment, the further compound is a steroid. In a further embodiment, the steroid is a corticosteroid. In even a further embodiment, the further compound is a glucocorticoid.

In even another embodiment, the further compound is cyclophosphamide (CYC), alone or in combination with one or more glucocorticoids.

In one combination therapy embodiment, the compound of the disclosure, or a pharmaceutically acceptable salt thereof, is administered concurrently or sequentially with one or more further active ingredients selected from one or more of those provided above. For example, the compound of Formula (I), or a pharmaceutically acceptable salt thereof, may be administered concurrently or sequentially with a further pharmaceutical composition for use as a medicament for the treatment of LN. The further pharmaceutical composition may be a medicament which the patient may already be prescribed (e.g., an existing standard or care medication), and may itself be a composition comprising one or more active ingredients selected from those defined above.

A compound of formula (I) or a pharmaceutically acceptable salt thereof can be synthesized by reacting a compound of formula (II),

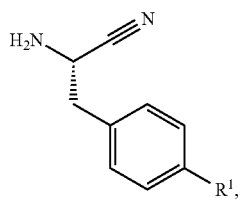

(II)

wherein R¹ is as defined in formula (I), with a compound of formula (III),

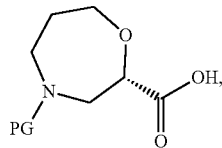

(III)

wherein PG represents a protecting group (e.g. tert-butoxycarbonyl), and optionally thereafter carrying out one or more of the following procedures:

converting a compound of formula (I) into another compound of formula (I);

removing any protecting groups; and/or forming a pharmaceutically acceptable salt.

The process is conveniently carried out in the presence of a base such as DiPEA or TEA and one or more activating agents such as EDCI, 2-pyridinol-1-oxide, or T3P. The reaction is conveniently carried out in an organic solvent such as DMF or DCM at a temperature, for example, in the range from 20° C. to 100° C., in particular at ambient temperature (25° C.).

Compounds of formula (II) may be prepared by reaction of a compound of formula (IV),

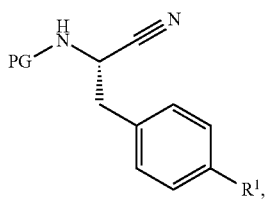

(IV)

wherein PG represents a protecting group (e.g. tert-butoxycarbonyl), with a suitable reagent to remove the protecting group PG. An example of a suitable reagent is formic acid.

Compounds of formula (IV) may be prepared by reacting a compound of formula (V),

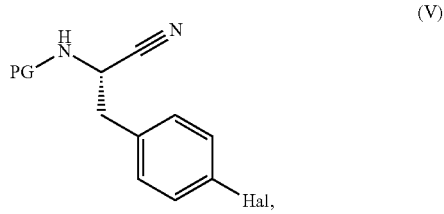

(V)

wherein PG represents a protecting group (e.g., tert-butoxycarbonyl) and Hal represents a halogen (e.g. I or Br), with a compound of formula (VI) or an ester thereof,

(VI)

wherein R¹ is as defined in formula (I), in the presence of a catalyst such as Pd(dppf)Cl₂·DCM or 1,1 bis(di-tert-butylphosphino)ferrocene palladium dichloride and a base such as potassium carbonate or sodium carbonate. The reaction is conveniently carried out in a solvent such as dioxane/water mixture or ACN/water mixture at a temperature, for example, in the range from 20° C. to 100° C., particularly at 75° C.

Compounds of formula (V) may be prepared from a compound of formula (VII),

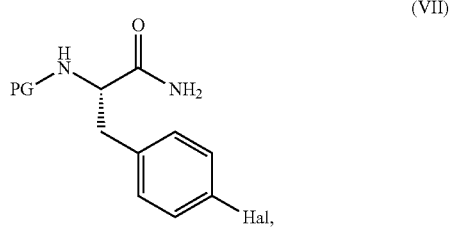

(VII)

in which PG represents a protecting group (e.g. tert-butoxycarbonyl) and Hal represents a halogen (e.g., I or Br), using standard literature procedures for the dehydration of an amide, for example with Burgess reagent, or with a reagent such as T3P with or without a base such as DiPEA, in a solvent such as DCM or DMF at a temperature in the range from −20° C. to 100° C., for example at 0° C.

Compounds of formula (VII) may be prepared by reacting a compound of formula (VIII),

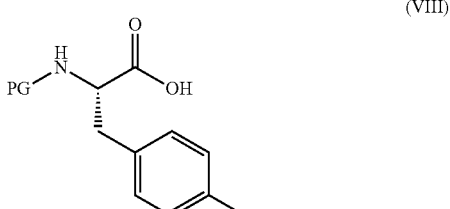

(VIII)

in which PG represents a protecting group (e.g. tert-butoxycarbonyl) and Hal represents a halogen (e.g., I or Br), with an aqueous ammonia solution, using standard literature procedures for the formation of an amide, for example, in the presence of a base such as N-ethyl-morpholine or DiPEA and an activating agent such as TBTU or T3P. The reaction is conveniently carried out in an organic solvent such as DMF, at a temperature in the range from −20° C. to 100° C., for example at 0° C.

Compounds of formula (VIII) are either commercially available, are known in the literature (e.g., from Tetrahedron: Asymmetry, 1998, 9, 503, incorporated by reference herein in its entirety for all purposes) or may be prepared using known techniques.

There is further provided a process for the preparation of a compound of formula (I), or a pharmaceutically acceptable salt thereof, as defined above which comprises reacting a compound of formula (IX),

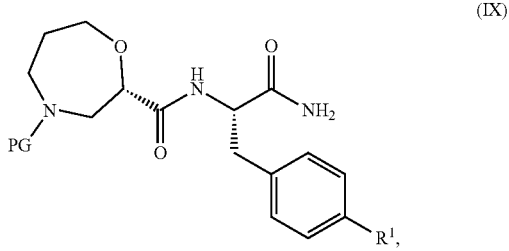

(IX)

wherein $R^1$ is as defined above and PG represents a protecting group (e.g. tert-butoxycarbonyl), using standard literature procedures for the dehydration of an amide, for example with Burgess reagent or with a reagent such as T3P with or without a base such as DiPEA, in a solvent such as DCM or DMF at a temperature in the range from −20° C. to 100° C., for example at 25° C., and thereafter reacting with a suitable reagent to remove the protecting group PG. An example of a suitable reagent is formic acid.

A compound of formula (IX) may be prepared by reacting a compound of formula (X), wherein PG represents a protecting group (e.g. tert-butoxycarbonyl),

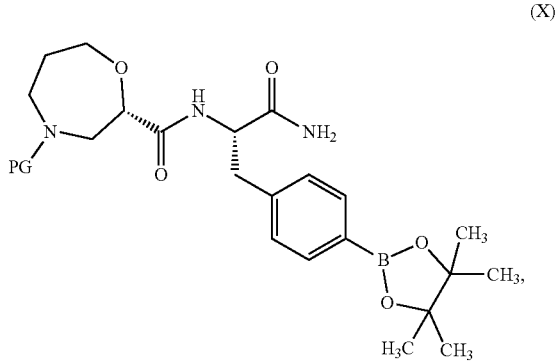

(X)

with a halide of formula (XI), wherein $R^1$ is defined as in formula (I), $R^1$—Br/I (XI), in the presence of a catalyst such as bis[bis(1,2-diphenylphosphino)ethane]palladium(0), or Pd(dppf)Cl$_2$ DCM, and a base such as potassium carbonate or sodium carbonate. The reaction is conveniently carried out in a solvent such as dioxane/water mixture or ACN/water mixture at a temperature, for example, in the range from 20° C. to 100° C., particularly at 80° C.

A compound of formula (X) may be prepared by reacting a compound of formula (XII), wherein PG represents a protecting group (e.g. tert-butoxycarbonyl),

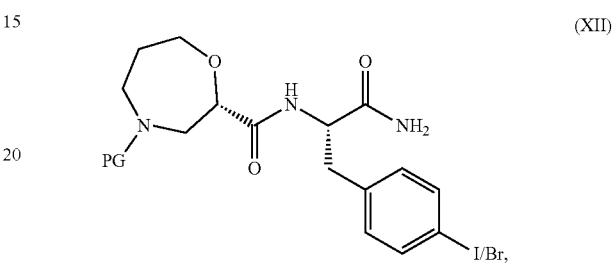

(XII)

with B$_2$Pin$_2$ in the presence of a suitable catalyst such as Pd(dppf)Cl$_2$·DCM and with or without 1,1'-bis(diphenylphosphino)ferrocene or 1,1-bis(di-tert-butylphosphino)ferrocene palladium dichloride, with a suitable salt such as potassium acetate, in a solvent such as DMSO at a temperature in the range 60° C. to 100° C., for example at 85° C.

A compound of formula (XII) may be prepared by reacting a compound of formula (XIII),

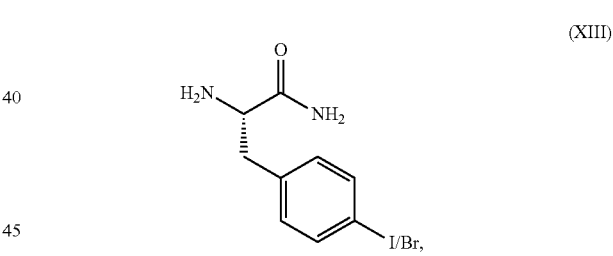

(XIII)

with a compound of formula (III),

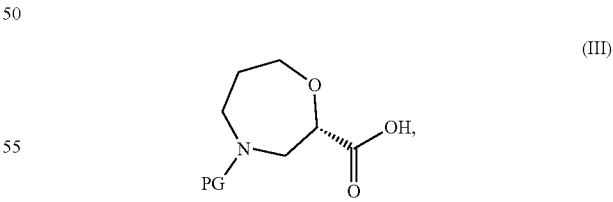

(III)

wherein PG represents a protecting group (e.g. tert-butoxycarbonyl) in the presence of a base such as DiPEA or TEA and an activating agent such as EDCI, 2-pyridinol-1-oxide, or T3P. The reaction is conveniently carried out in an organic solvent such as DMF or DCM at a temperature, for example, in the range from 20° C. to 100° C., in particular at ambient temperature (25° C.).

Compounds of formula (XIII) may be prepared by reacting a compound of formula (XIV),

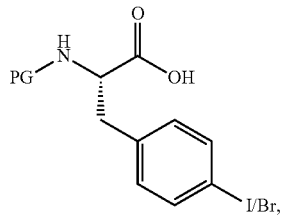
(XIV)

in which PG is as defined in formula (VII), with an aqueous ammonia solution, using standard literature procedures for the formation of an amide, for example, in the presence of a base such as N-ethyl-morpholine or DiPEA and an activating agent such as a "uronium" reagent (for example TBTU), or T3P. The reaction is conveniently carried out in an organic solvent such as DMF, at a temperature in the range from −20° C. to 100° C., for example at 0° C.

A compound of formula (IX) may be prepared by reacting a compound of formula (XII) wherein PG represents a protecting group (e.g. tert-butoxycarbonyl), with a compound of formula (VI) or a boronate ester thereof, in the presence of a catalyst such as bis[bis(1,2-diphenylphosphino)ethane]palladium(0) or Pd(dppf)Cl$_2$·DCM and a base such as potassium carbonate or sodium carbonate. The reaction is conveniently carried out in a solvent such as dioxane/water or ACN/water mixture at a temperature, for example, in the range from 20° C. to 100° C., particularly at 80° C.

There is further provided a process for the preparation of a compound of formula (I), or a pharmaceutically acceptable salt thereof, as defined above which comprises reacting a compound of formula (XV),

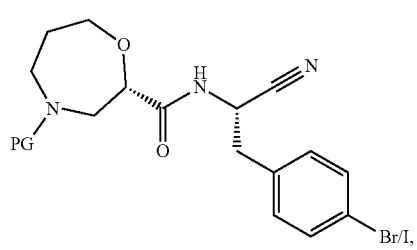
(XV)

wherein PG represents a protecting group (e.g. tert-butoxycarbonyl), with a compound of formula (VI) or an ester thereof, wherein R$^1$ is as defined in formula (I), in the presence of a catalyst such as Pd(dppf)Cl$_2$·DCM or 1,1 bis(di-tert-butylphosphino)ferrocene palladium dichloride and a base such as potassium carbonate or sodium carbonate. The reaction is conveniently carried out in a solvent such as dioxane/water mixture or ACN/water mixture at a temperature, for example, in the range from 20° C. to 100° C., particularly at 75° C., and thereafter reacting with a suitable reagent to remove the protecting group PG. An example of a suitable reagent is formic acid.

Compounds of formula (XV) may be prepared from compounds of formula (XII) using standard procedures for the dehydration of an amide, for example with Burgess reagent or a reagent such as TBTU or T3P with or without a base such as DiPEA, in a solvent such as DCM or DMF at a temperature in the range from −20° C. to 100° C., for example at 25° C.

There is further provided a process for the preparation of a compound of formula (I) or a pharmaceutically acceptable salt thereof as defined above which comprises reacting a compound of formula (XVI),

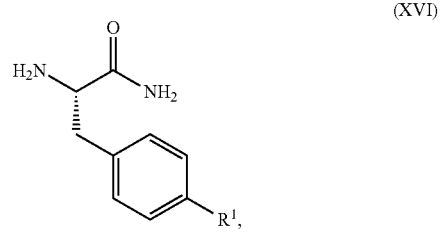
(XVI)

wherein R$^1$ is as defined in formula (I), with a compound of formula (III), conveniently carried out in the presence of a base such as DiPEA or TEA and one or more activating agents such as EDCI, 2-pyridinol-1-oxide, or T3P, followed by a dehydrating reagent such as T3P. The reaction is conveniently carried out in an organic solvent such as DMF or DCM at a temperature, for example, in the range from 20° C. to 100° C., in particular at ambient temperature (25° C.).

Compounds of formula (XVI) can be prepared from reacting compounds of formula (VII) with compounds of formula (VI) or an ester thereof, wherein R$^1$ is as defined in formula (I), in the presence of a catalyst such as Pd(dppf)Cl$_2$·DCM or 1,1 bis(di-tert-butylphosphino)ferrocene palladium dichloride and a base such as potassium carbonate or sodium carbonate. The reaction is conveniently carried out in a solvent such as dioxane/water mixture or ACN/water mixture at a temperature, for example, in the range from 20° C. to 100° C., particularly at 75° C., followed by deprotection of PG.

A compound of formula (III),

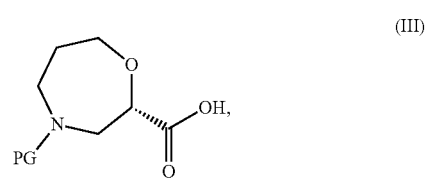
(III)

wherein PG represents a protecting group (e.g. tert-butoxycarbonyl) is either commercially available, or may be prepared from a compound of formula (XVII),

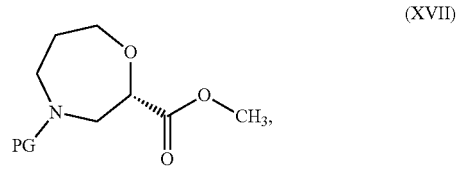
(XVII)

using literature procedures for mild ester hydrolysis (e.g. from Tetr. Lett., 2007, 48, 2497, incorporated by reference herein in its entirety for all purposes), for example with LiBr and a base such as TEA, in a solvent such as ACN/water mixture, for example at 25° C.

A compound of formula (XVII), wherein PG represents a protecting group (e.g. tert-butoxycarbonyl), may be prepared from a compound of formula (XVIII),

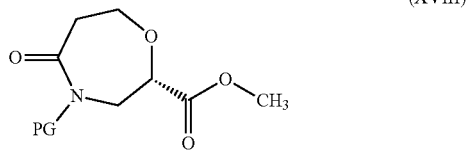

using a reducing agent, for example BH$_3$-DMS, in a solvent such as THF, at a temperature in the range from 0 to 40° C., for example at 25° C.

A compound of formula (XVIII), where PG represents a protecting group (e.g. tert-butoxycarbonyl), may be prepared from a compound of formula (XIX), using a biocatalytic transformation for chemoselective lactam formation, e.g., using a lipase such as Novozym 435, in a solvent such as an ether, e.g., dioxane, at a temperature in the range from 0 to 80° C., for example at 55° C., followed by conditions for introduction of the protecting group PG.

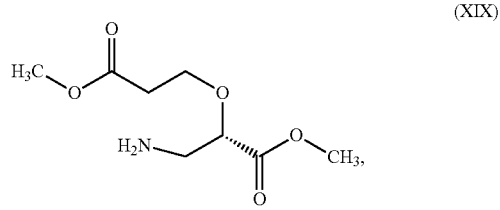

A compound of formula (XIX) may be prepared from a compound of formula (XX),

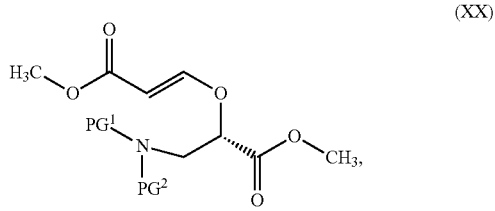

wherein PG$^1$ and PG$^2$ are protecting groups (e.g., benzyl), using conditions for hydrogenation, for example using H$_2$ (g), and a reagent such as palladium dihydroxide on carbon, in a solvent such as methanol or dioxane, under a pressure of for example 10 bar, at a temperature in the range from 25 to 80° C., for example at 40° C.

A compound of formula (XX), wherein PG$^1$ and PG$^2$ are protecting groups (e.g., benzyl), may be prepared from a compound of formula (XXI),

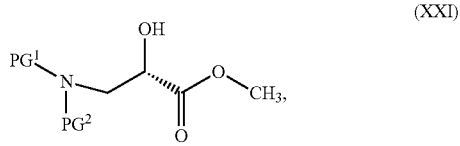

wherein PG$^1$ and PG$^2$ are protecting groups (e.g. benzyl), using conditions for Oxa-Michael reaction, reacting with methyl propynoate, in presence of a base such as 4-methylmorpholine, in a solvent such as toluene, at a temperature in the range from 0 to 100° C., for example at 25° C.

A compound of formula (XXI), wherein PG$^1$ and PG$^2$ are protecting groups (e.g. benzyl), may be prepared from reacting a diprotected benzyl amine (e.g., dibenzylamine) with (S)-methyl oxirane-2-carboxylate, in a solvent such as ethanol, at a temperature in the range from 0 to 78° C., for example at 70° C.

Alternatively, a compound of formula (III),

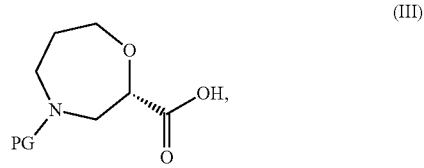

wherein PG represents a protecting group (e.g. tert-butoxycarbonyl) may be prepared from oxidation of a compound of formula (XXII),

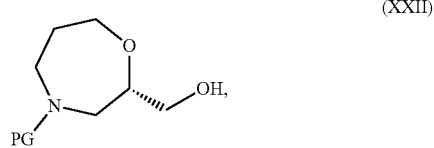

for example, using reagents such as TEMPO, and sodium hypochlorite, optionally in presence of a salt such as sodium bromide, in a solvent such as DCM/water, and in presence of a buffer such as NaHCO$_3$, and a phase transfer catalyst such as tetrabutylammonium bisulphate, at a temperature in the range from 0 to 100° C., e.g., at 25° C.

A compound of formula (XXII), wherein PG represents a protecting group (e.g., tert-butoxycarbonyl) may be prepared from a compound of formula (XXIII),

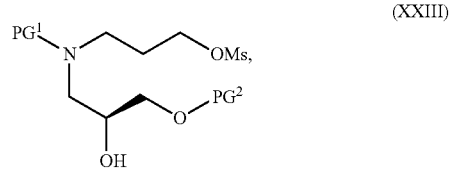

wherein PG$^1$ and PG$^2$ are protecting groups (e.g. benzyl), reacting with a base such as sodium hydride, in a solvent such as THF, at a temperature in the range from 0 to 60° C., e.g., 25° C., followed by interconversion of protecting groups PG, PG$^1$ and PG$^2$, as defined in formula (XXII) and (XXIII).

A compound of formula (XXIII), wherein PG$^1$ and PG$^2$ are protecting groups (e.g., benzyl), may be prepared from reacting protected 3-aminopropanol (e.g. N-benzyl-3-aminopropanol) with (S)-2-((benzyloxy)methyl)oxirane, in a solvent such as ethanol or propanol, at a temperature in the range from 0 to 70° C., for example at 40° C., followed by reacting the crude product with methanesulfonyl chloride, in prescence of a base such as DiPEA, in a solvent such as DCM, at a temperature in the range from −10 to 25° C., e.g., −5° C.

Compounds of formula (VI) or an ester thereof, (VIII), (XI) and (XIV) are either commercially available, are known in the literature or may be prepared using known techniques.

It will be appreciated by those skilled in the art that in the processes of the present disclosure certain functional groups such as hydroxyl or amino groups in the reagents may need to be protected by protecting groups. Thus, the preparation of the compounds of formula (I) may involve, at an appropriate stage, the removal of one or more protecting groups.

The skilled person will recognise that at any stage of the preparation of the compounds of formula (I), mixtures of isomers (e.g., racemates) of compounds corresponding to any of formulae (II)-(V), (VII)-(X) and (XXII)-(XVI) may be utilized. At any stage of the preparation, a single stereoisomer may be obtained by isolating it from a mixture of isomers (e.g., a racemate) using, for example, chiral chromatographic separation.

The protection and deprotection of functional groups is described in 'Protective Groups in Organic Synthesis', 4$^{th}$ Ed, T. W. Greene and P. G. M. Wuts, Wiley (2006) and 'Protecting Groups', 3$^{rd}$ Ed P. J. Kocienski, Georg Thieme Verlag (2005), incorporated by reference herein in its entirety for all purposes.

As provided throughout, according to the methods provided herein, a compound of formula (I) can be administered as a pharmaceutically acceptable salt. A pharmaceutically acceptable salt of a compound of formula (I) may be advantageous due to one or more of its chemical or physical properties, such as stability in differing temperatures and humidities, or a desirable solubility in $H_2O$, oil, or other solvent. In some instances, a salt may be used to aid in the isolation or purification of the compound of formula (I).

Where the compound of formula (I) is sufficiently acidic, pharmaceutically acceptable salts include, but are not limited to, an alkali metal salt, e.g., Na or K, an alkali earth metal salt, e.g., Ca or Mg, or an organic amine salt. Where the compound of formula (I) is sufficiently basic, pharmaceutically acceptable salts include, but are not limited to, inorganic or organic acid addition salts.

There may be more than one cation or anion depending on the number of charged functions and the valency of the cations or anions.

For reviews on suitable salts, and pharmaceutically acceptable salts amenable for use herein, see Berge et al., *J. Pharm. Sci.,* 1977, 66, 1-19 or "Handbook of Pharmaceutical Salts: Properties, selection and use", P. H. Stahl, P. G. Vermuth, IUPAC, Wiley-VCH, 2002, incorporated by reference herein in its entirety for all purposes.

The compounds of formula (I) may form mixtures of its salt and co-crystal forms. It is also to be understood that the methods provided herein can employ such salt/co-crystal mixtures of the compound of formula (I).

Salts and co-crystals may be characterized using well known techniques, for example X-ray powder diffraction, single crystal X-ray diffraction (for example to evaluate proton position, bond lengths or bond angles), solid state NMR, (to evaluate for example, C, N or P chemical shifts) or spectroscopic techniques (to measure for example, O—H, N—H or COOH signals and IR peak shifts resulting from hydrogen bonding).

It is also to be understood that certain compounds of formula (I) may exist in solvated form, e.g., hydrates, including solvates of a pharmaceutically acceptable salt of a compound of formula (I).

In one embodiment, certain compounds of formula (I) may exist as racemates and racemic mixtures, single enantiomers, individual diastereomers and diastereomeric mixtures. It is to be understood that the present disclosure encompasses all such isomeric forms. Certain compounds of formula (I) may also contain linkages (e.g., carbon-carbon bonds, carbon-nitrogen bonds such as amide bonds) wherein bond rotation is restricted about that particular linkage, e.g. restriction resulting from the presence of a ring bond or double bond. Accordingly, it is to be understood that the methods provided herein can employ such isomers. Certain compound of formula (I) may also contain multiple tautomeric forms. It is to be understood that the present disclosure encompasses all such tautomeric forms. Stereoisomers may be separated using conventional techniques, e.g. chromatography or fractional crystallization, or the stereoisomers may be made by stereoselective synthesis.

In a further embodiment, the compounds of formula (I) encompasses any isotopically-labeled (or "radio-labelled") derivatives of a compound of formula (I). Such a derivative is a derivative of a compound of formula (I) wherein one or more atoms are replaced by an atom having an atomic mass or mass number different from the atomic mass or mass number typically found in nature. Examples of radionuclides that may be incorporated include $^2$H (also written as "D" for deuterium). As such, in one embodiment, a compound of formula (I) is provided where one or more hydrogen atoms are replaced by one or more deuterium atoms; and the deuterated compound is used in one of the methods provided herein for treating LN.

In a further embodiment, the compounds of formula (I) may be administered in the form of a prodrug which is broken down in the human or animal body to give a compound of the formula (I). Examples of prodrugs include in vivo hydrolysable esters of a compound of the formula (I).

An in vivo hydrolysable (or cleavable) ester of a compound of the formula (I) that contains a carboxy or a hydroxy group is, for example, a pharmaceutically acceptable ester which is hydrolyzed in the human or animal body to produce the parent acid or alcohol. For examples of ester prodrugs derivatives, see: *Curr. Drug. Metab.* 2003, 4, 461, incorporated by reference herein in its entirety for all purposes.

Various other forms of prodrugs are known in the art, and can be used in the methods provided herein. For examples of prodrug derivatives, see: *Nature Reviews Drug Discovery* 2008, 7, 255, the disclosure of which is incorporated by reference herein in its entirety for all purposes.

Example

The present invention is further illustrated by reference to the following Example. However, it should be noted that these Examples, like the embodiments described above, are illustrative and are not to be construed as restricting the scope of the invention in any way.

Effect of INS1007 in an Accelerated Lupus Nephritis Model in Mice

INS1007 as a potential treatment for LN was assessed. 10-11 week old female New Zealand Black/New Zealand White F1 (NZB/WF1) mice (Jackson Laboratory) were subjected to a single injection of an adenovirus expressing IFNα5 (Ad-IFNα5, BioXcell, cat #BE0241, clone AR1-5A3) to accelerate the clinical manifestations of LN. FIG. 1 provides a schematic overview of the study design.

Treatment groups and dosing schedule are provided in Table 1. The duration of the study was 8 weeks from Ad-IFNα5 injection.

TABLE 1

| Group | Size of Group | Treatment | Dose volume/ route | Dosing schedule | Dosing initiation |
|---|---|---|---|---|---|
| 1 | n = 16 | Vehicle | 10 mL/kg PO | Twice daily | Week 2 |
| 2 | n = 16 | INS1007 (0.1 mg/kg) | 10 mL/kg PO | Twice daily | Week 2 |
| 3 | n = 16 | INS1007 (1 mg/kg) | 10 mL/kg PO | Twice daily | Week 2 |
| 4 | n = 16 | INS1007 (10 mg/kg) | 10 mL/kg PO | Twice daily | Week 2 |
| 5 | n = 16 | IFNαR Ab | 5 mL/kg IP | Twice weekly | Week 3 |

IFNαR Ab - IFNα receptor antibody;
PO - Per os (oral);
IP - intraperitoneal

Urine and blood collection was carried out at baseline (immediately after Ad-IFNα5 injection), and at weeks 2, 4, 6 and 8. Total protein (by chemstick), albumin (by ELISA) and creatinine (by a colorimetric assay kit) was measured in urine and blood urea nitrogen (BUN) was measured in plasma.

Figure 3:
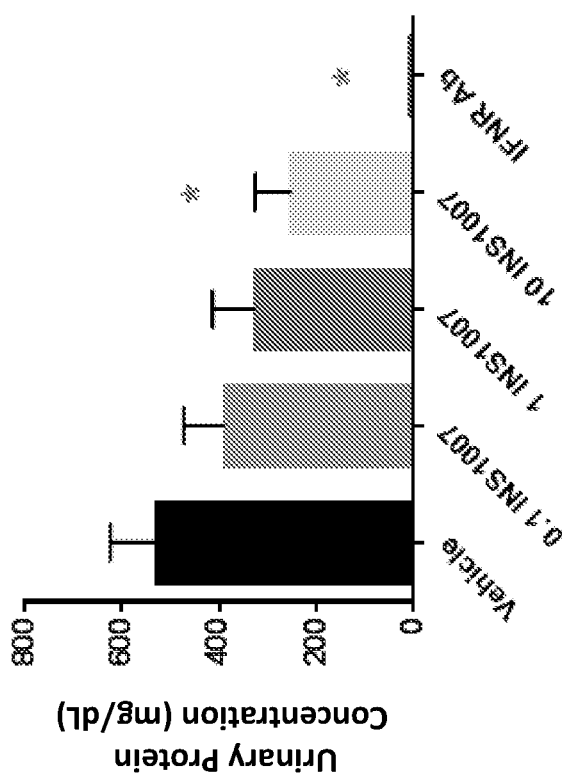
FIG. 3 is a graph of the urinary protein concentration at week 8 (mg/dL) for the various treatment groups of NZB/WF1 mice subjected to the accelerated LN model. *P<0.05 vs. vehicle as measured by ANOVA.
Figure 2:
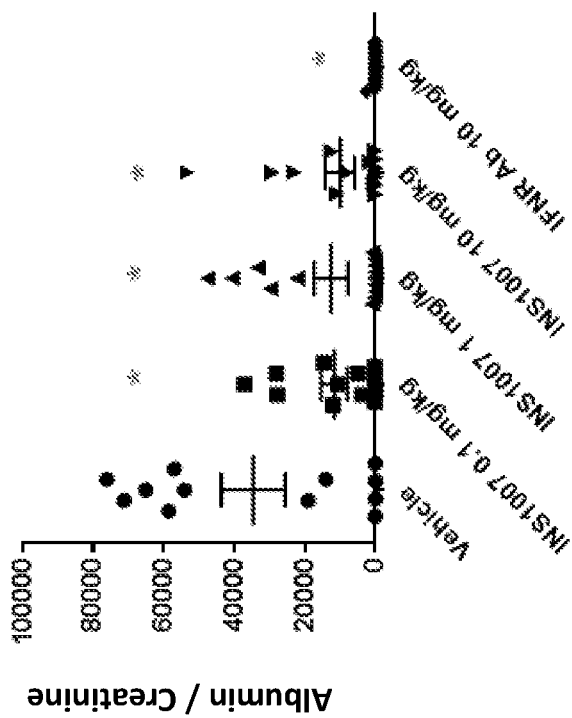
FIG. 2 is a graph of the albumin/creatinine ratio in urine at week 8 for the various treatment groups of NZB/WF1 mice subjected to the accelerated LN model. *P<0.05 vs. vehicle as measured by ANOVA.
Figure 5:
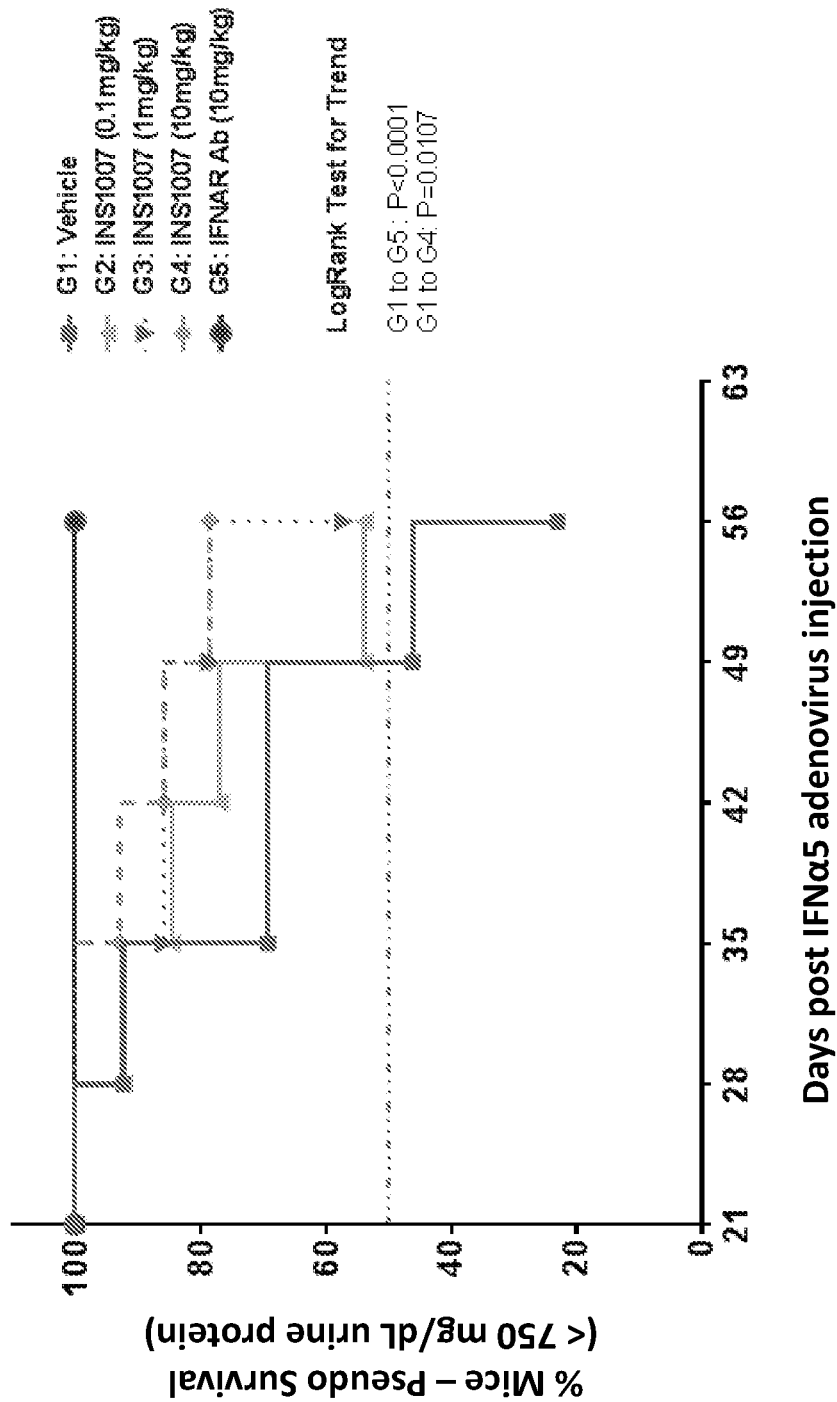
FIG. 5 is a pseudo survival curve for the various mouse treatment groups as a function of days post model initiation (IFNα5 adenovirus injection). Pseudo-survival is indicated by a urine protein level of <750 mg/dL.

Albumin/creatinine ratio for the different animal groups at week 8 are provided in FIG. 2. Mice treated with INS1007 demonstrated a decrease in urinary protein concentration (mg/dL) in a dose dependent manner (FIG. 3). Lower urinary protein levels are correlated with decrease in kidney damage. Total protein levels were also assessed by generating a pseudo-survival curve (FIG. 5). Here, animals were reported to "survive" if their total protein levels in urine were less than 750 mg/dL. As can be seen in the figure, INS1007 increased "pseudo-survival" (and decreased total protein concentration) in a dose dependent manner.

Figure 4:
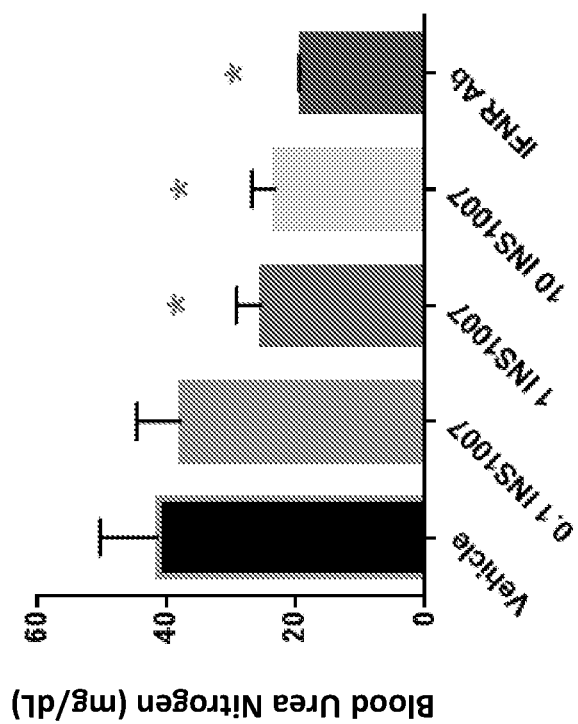
FIG. 4 is a graph of blood urea nitrogen (BUN) levels at week 6 for the various treatment groups of NZB/WF1 mice subjected to the accelerated LN model. *P<0.05 vs. vehicle as measured by ANOVA.

BUN (mg/dL) levels 6 weeks after model induction are reported at FIG. 4. The data demonstrate that BUN levels decreased in animals treated with INS1007 in a dose dependent matter (FIG. 4). Lower BUN levels are correlated with increased kidney function.

Figure 6:
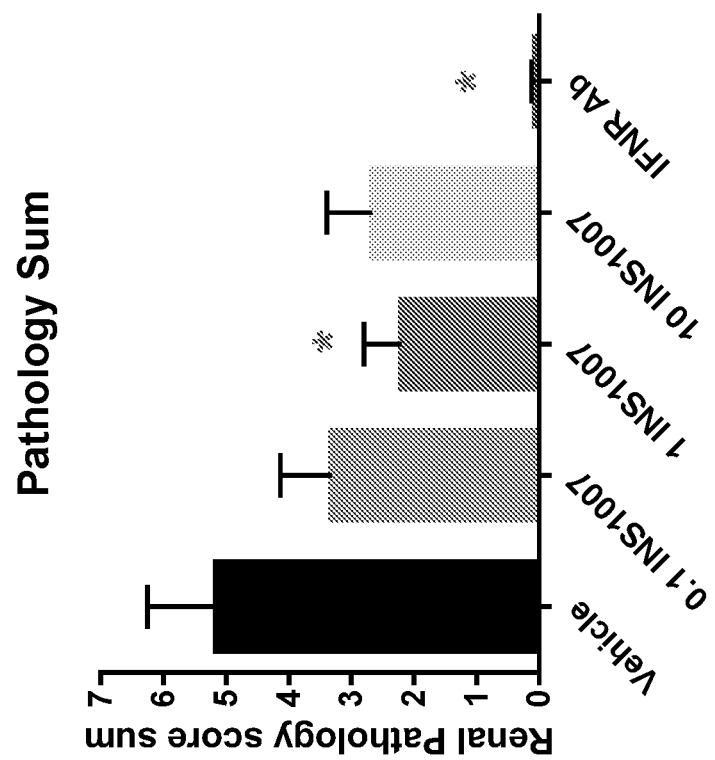
FIG. 6 is a graph of the renal pathology score sum (summed from individual scores for (i) glomerulonephritis, (ii) tubular protein and (iii) nephropathy) for the various treatment groups. *P<0.05 vs. vehicle as measured by ANOVA.
Figure 8:
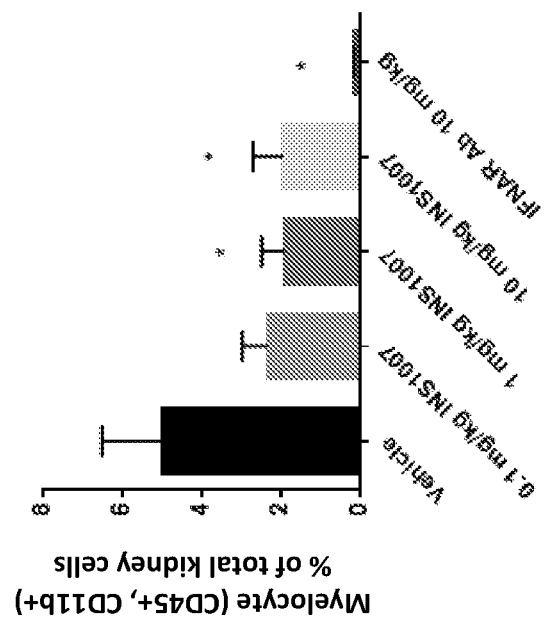
FIG. 8 is a graph of the myelocyte percent of total kidney cells (as measured by FACS, CD45+, CD11b+) for the various treatment groups. *P<0.05 vs. vehicle as measured by ANOVA.
Figure 7:
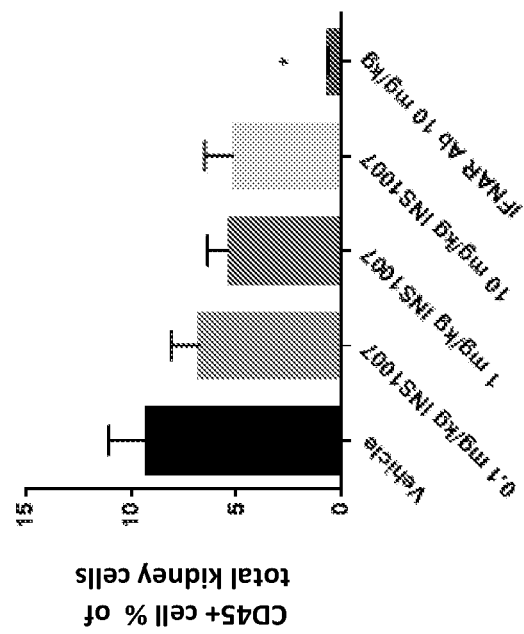
FIG. 7 is a graph of the CD45+ cell percent of total kidney cells (as measured by FACS) for the various treatment groups. *P<0.05 vs. vehicle as measured by ANOVA.
Figure 10:
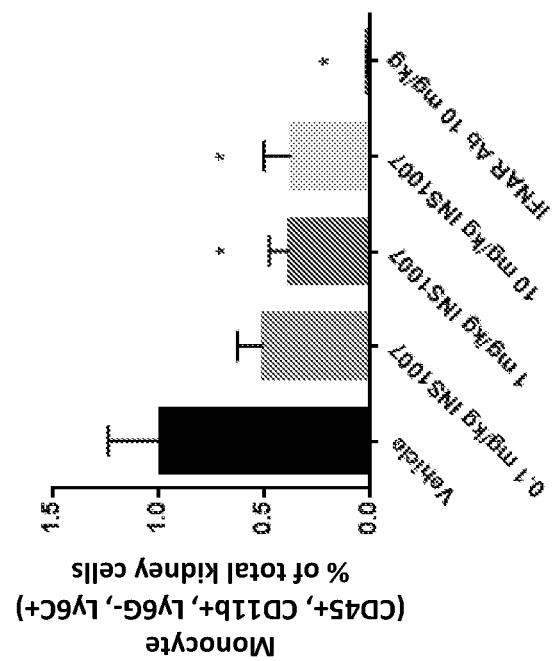
FIG. 10 is a graph of the monocyte percent of total kidney cells (as measured by FACS, CD45+, CD11b+, Ly6G−, Ly6C+) for the various treatment groups. *P<0.05 vs. vehicle as measured by ANOVA.
Figure 9:
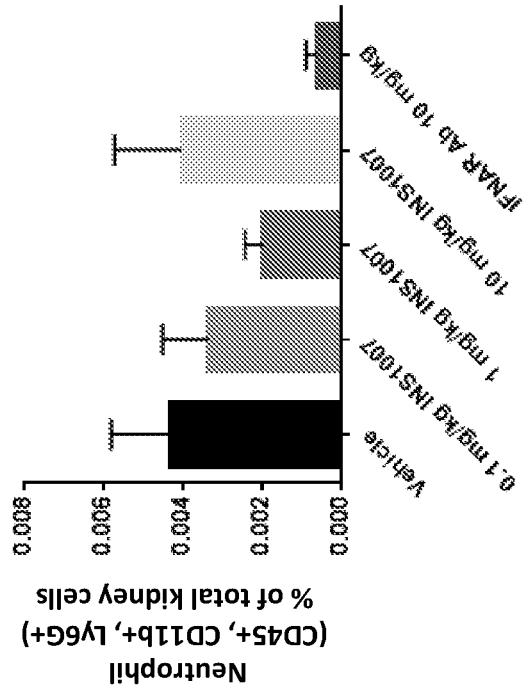
FIG. 9 is a graph of the neutrophil percent of total kidney cells (as measured by FACS, CD45+, CD11b+, Ly6G+) for the various treatment groups.
Figure 12:
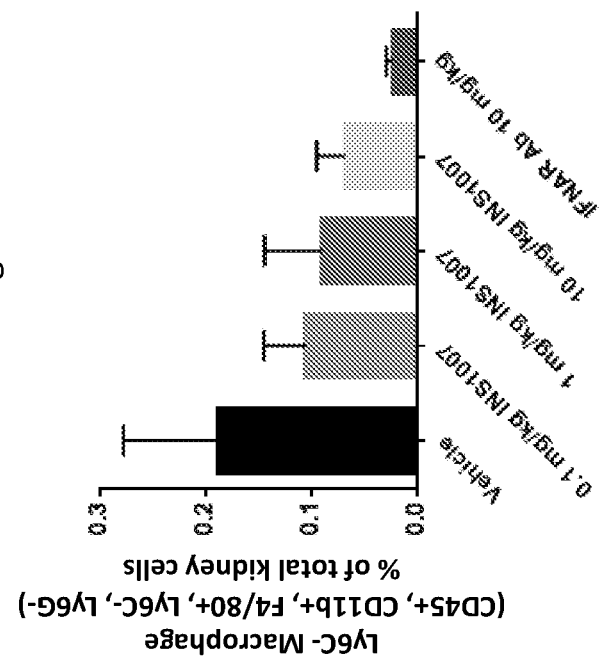
FIG. 12 is a graph of the Ly6C− macrophage percent of total kidney cells (as measured by FACS, CD45+, CD11b+, F4/80+, Ly6C−, Ly6G−) for the various treatment groups.
Figure 11:
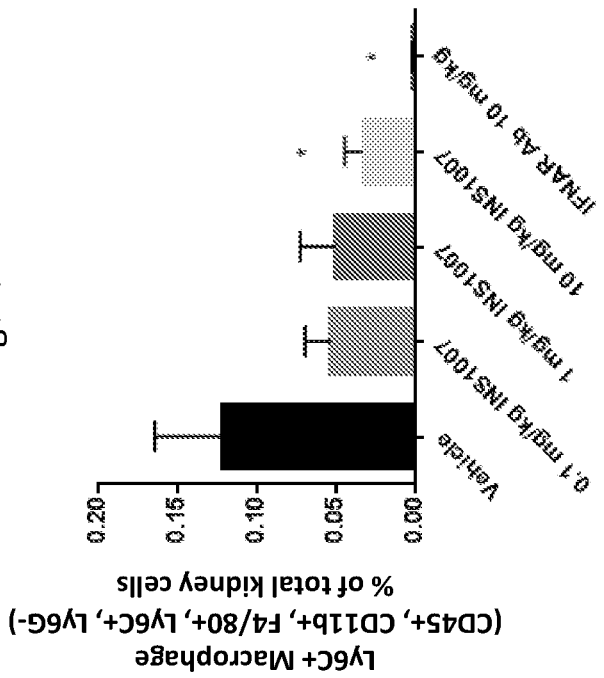
FIG. 11 is a graph of the Ly6C+ macrophage percent of total kidney cells (as measured by FACS, CD45+, CD11b+, F4/80+, Ly6C+, Ly6G−) for the various treatment groups. *P<0.05 vs. vehicle as measured by ANOVA.
Figure 13:
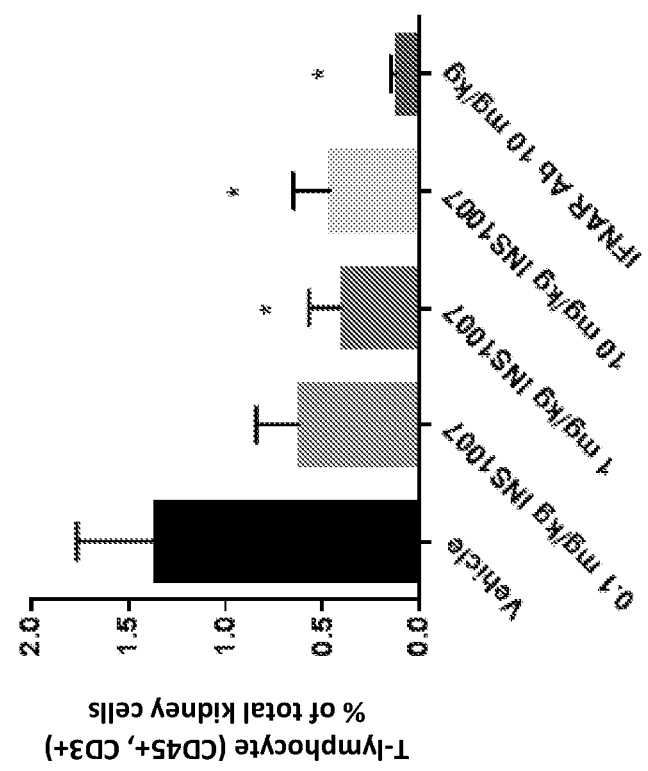
FIG. 13 is a graph of the T-lymphocyte percent of total kidney cells (as measured by FACS, CD45+, CD3+) for the various treatment groups. *P<0.05 vs. vehicle as measured by ANOVA.

Animals were sacrificed at 8 weeks and the left kidney of each animal was used for histopathology analysis. Pathology scores are summed from individual scores of three aspects: glomerulonephritis, tubular protein and nephropathy and were scored by a Certified Veterinary Pathologist. The results of the pathology analysis are provided in FIG. 6. FIG. 6 shows that INS1007 decreased renal pathology as compared to vehicle control.

The right kidneys of each animal were used for FACS analysis. Right kidneys were digested and subjected to Percoll centrifugation, fixable-viability-dye and surface staining for the following markers: CD45, CD3, CD11b, F4/80, Ly6G and Ly6C. Results of FACS are provided at FIGS. 7-13. The figures shows INS1007 significantly decreased a variety of immune cells, including myelocytes, $Ly6C^+$ monocyte, $Ly6C^+$ macrophages and T cells, which might possibly have played a pro-inflammatory role in nephritis pathogenesis.

All, documents, patents, patent applications, publications, product descriptions, and protocols which are cited throughout this application are incorporated herein by reference in their entireties for all purposes.

The embodiments illustrated and discussed in this specification are intended only to teach those skilled in the art the best way known to the inventors to make and use the invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

The invention claimed is:

1. A method for treating lupus nephritis (LN) in a patient in need of treatment, comprising, administering to the patient a pharmaceutical composition comprising an effective amount of a compound of formula (I), or a pharmaceutically acceptable salt thereof,

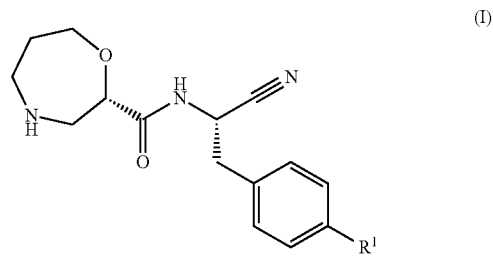

(I)

wherein,
$R^1$ is

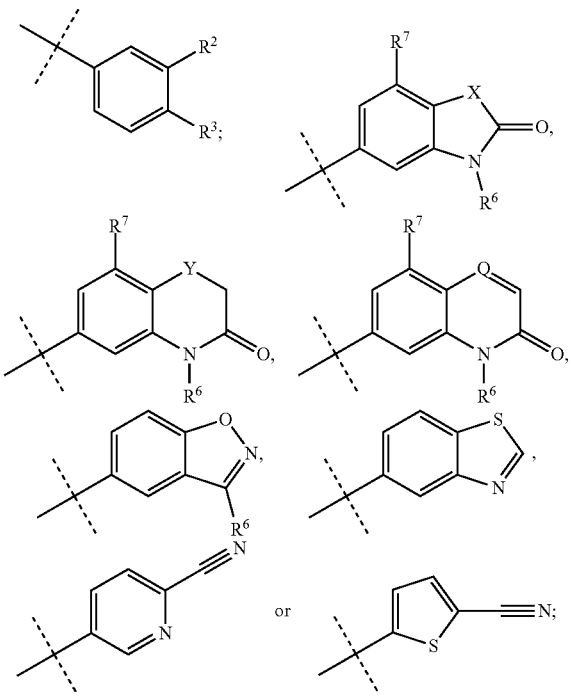

$R^2$ is hydrogen, F, Cl, Br, $OSO_2C_{1-3}$alkyl, or $C_{1-3}$alkyl;
$R^3$ is hydrogen, F, Cl, Br, CN, $CF_3$, $SO_2C_{1-3}$alkyl, $CONH_2$ or $SO_2NR^4R^5$, wherein $R^4$ and $R^5$ together with the nitrogen atom to which they are attached form an azetidine, pyrrolidine or piperidine ring; or
$R^6$ is $C_{1-3}$alkyl, optionally substituted by 1, 2 or 3 F and/or optionally by OH, $OC_{1-3}$alkyl, $N(C_{1-3}$alkyl$)_2$, cyclopropyl, or tetrahydropyran;

R⁷ is hydrogen, F, Cl or CH₃;
X is O, S or CF₂;
Y is O or S; and
Q is CH or N.

2. The method of claim 1, wherein, R¹ is

[chemical structure: benzoxazolone ring with R⁷ at 4-position, tert-butyl-like substituent (dashed bonds) at 6-position, X in ring, and R⁶ on N]

3. The method of claim 1, wherein, X is O; R⁶ is C₁₋₃alkyl; and R⁷ is hydrogen.

4. The method of claim 1, wherein the compound of formula (I) is selected from the group consisting of
(2S)—N-[(1S)-1-Cyano-2-(4'-cyanobiphenyl-4-yl)ethyl]-1,4-oxazepane-2-carboxamide;
(2S)—N-{(1S)-1-Cyano-2-[4-(3-methyl-2-oxo-2,3-dihydro-1,3-benzoxazol-5-yl)phenyl]ethyl}-1,4-oxazepane-2-carboxamide;
(2S)—N-{(1S)-1-Cyano-2-[4-(3,7-dimethyl-2-oxo-2,3-dihydro-1,3-benzoxazol-5-yl)phenyl]ethyl}-1,4-oxazepane-2-carboxamide;
4'-[(2S)-2-Cyano-2-{[(2S)-1,4-oxazepan-2-ylcarbonyl]amino}ethyl]biphenyl-3-yl methanesulfonate;
(2S)—N-{(1S)-1-Cyano-2-[4-(3-methyl-1,2-benzoxazol-5-yl)phenyl]ethyl}-1,4-oxazepane-2-carboxamide;
(2S)—N-{(1S)-1-Cyano-2-[4'-(trifluoromethyl)biphenyl-4-yl]ethyl}-1,4-oxazepane-2-carboxamide;
(2S)—N-[(1S)-1-Cyano-2-(3',4'-difluorobiphenyl-4-yl)ethyl]-1,4-oxazepane-2-carboxamide;
(2S)—N-{(1S)-1-Cyano-2-[4-(6-cyanopyridin-3-yl)phenyl]ethyl}-1,4-oxazepane-2-carboxamide;
(2S)—N-{(1S)-1-Cyano-2-[4-(4-methyl-3-oxo-3,4-dihydro-2H-1,4-benzothiazin-6-yl)phenyl]ethyl}-1,4-oxazepane-2-carboxamide;
(2S)—N-{(1S)-1-Cyano-2-[4-(3-ethyl-7-methyl-2-oxo-2,3-dihydro-1,3-benzoxazol-5-yl)phenyl]ethyl}-1,4-oxazepane-2-carboxamide;
(2S)—N-[(1S)-1-Cyano-2-{4-[3-(2-hydroxy-2-methylpropyl)-2-oxo-2,3-dihydro-1,3-benzoxazol-5-yl]phenyl}ethyl]-1,4-oxazepane-2-carboxamide;
(2S)—N-[(1S)-1-Cyano-2-{4-[3-(2,2-difluoroethyl)-7-fluoro-2-oxo-2,3-dihydro-1,3-benzoxazol-5-yl]phenyl}ethyl]-1,4-oxazepane-2-carboxamide;
(2S)—N-[(1S)-1-Cyano-2-(4-{3-[2-(dimethylamino)ethyl]-2-oxo-2,3-dihydro-1,3-benzoxazol-5-yl}phenyl)ethyl]-1,4-oxazepane-2-carboxamide;
(2S)—N-{(1S)-1-Cyano-2-[4-(3,3-difluoro-1-methyl-2-oxo-2,3-dihydro-1H-indol-6-yl)phenyl]ethyl}-1,4-oxazepane-2-carboxamide;
(2S)—N-{(1S)-1-Cyano-2-[4-(7-fluoro-3-methyl-2-oxo-2,3-dihydro-1,3-benzoxazol-5-yl)phenyl]ethyl}-1,4-oxazepane-2-carboxamide;
(2S)—N-{(1S)-1-Cyano-2-[4-(3-ethyl-2-oxo-2,3-dihydro-1,3-benzoxazol-5-yl)phenyl]ethyl}-1,4-oxazepane-2-carboxamide;
(2S)—N-[(1S)-1-Cyano-2-{4-[3-(cyclopropylmethyl)-2-oxo-2,3-dihydro-1,3-benzoxazol-5-yl]phenyl}ethyl]-1,4-oxazepane-2-carboxamide;
(2S)—N-[(1S)-1-Cyano-2-{4-[3-(2-methoxyethyl)-2-oxo-2,3-dihydro-1,3-benzothiazol-5-yl]phenyl}ethyl]-1,4-oxazepane-2-carboxamide;
(2S)—N-[(1S)-1-Cyano-2-{4-[2-oxo-3-(propan-2-yl)-2,3-dihydro-1,3-benzoxazol-5-yl]phenyl}ethyl]-1,4-oxazepane-2-carboxamide;
(2S)—N-{(1S)-1-Cyano-2-[4-(4-methyl-3-oxo-3,4-dihydro-2H-1,4-benzoxazin-6-yl)phenyl]ethyl}-1,4-oxazepane-2-carboxamide;
(2S)—N-[(1S)-1-Cyano-2-{4-[3-(2-methoxyethyl)-2-oxo-2,3-dihydro-1,3-benzoxazol-5-yl]phenyl}ethyl]-1,4-oxazepane-2-carboxamide;
(2S)—N-{(1S)-1-Cyano-2-[4-(5-cyanothiophen-2-yl)phenyl]ethyl}-1,4-oxazepane-2-carboxamide;
(2S)—N-[(1S)-2-(4'-Carbamoyl-3'-fluorobiphenyl-4-yl)-1-cyanoethyl]-1,4-oxazepane-2-carboxamide;
(2S)—N-{(1S)-1-Cyano-2-[4-(1-methyl-2-oxo-1,2-dihydroquinolin-7-yl)phenyl]ethyl}-1,4-oxazepane-2-carboxamide;
(2S)—N-[(1S)-1-Cyano-2-{4-[2-oxo-3-(tetrahydro-2H-pyran-4-ylmethyl)-2,3-dihydro-1,3-benzoxazol-5-yl]phenyl}ethyl]-1,4-oxazepane-2-carboxamide;
(2S)—N-{(1S)-2-[4-(7-Chloro-3-methyl-2-oxo-2,3-dihydro-1,3-benzoxazol-5-yl)phenyl]-1-cyanoethyl}-1,4-oxazepane-2-carboxamide;
(2S)—N-[(1S)-1-Cyano-2-{4-[3-(2,2-difluoroethyl)-2-oxo-2,3-dihydro-1,3-benzoxazol-5-yl]phenyl}ethyl]-1,4-oxazepane-2-carboxamide;
(2S)—N-[(1S)-1-Cyano-2-{4-[2-oxo-3-(2,2,2-trifluoroethyl)-2,3-dihydro-1,3-benzoxazol-5-yl]phenyl}ethyl]-1,4-oxazepane-2-carboxamide;
(2S)—N-{(1S)-1-Cyano-2-[4-(3-methyl-2-oxo-2,3-dihydro-1,3-benzothiazol-5-yl)phenyl]ethyl}-1,4-oxazepane-2-carboxamide;
(2S)—N-{(1S)-1-Cyano-2-[4'-(methylsulfonyl)biphenyl-4-yl]ethyl}-1,4-oxazepane-2-carboxamide;
(2S)—N-{(1S)-2-[4'-(Azetidin-1-ylsulfonyl)biphenyl-4-yl]-1-cyanoethyl}-1,4-oxazepane-2-carboxamide;
(2S)—N-[(1S)-1-Cyano-2-(4'-fluorobiphenyl-4-yl)ethyl]-1,4-oxazepane-2-carboxamide;
(2S)—N-{(1S)-2-[4-(1,3-Benzothiazol-5-yl)phenyl]-1-cyanoethyl}-1,4-oxazepane-2-carboxamide; and
(2S)—N-[(1S)-1-Cyano-2-(4'-cyanobiphenyl-4-yl)ethyl]-1,4-oxazepane-2-carboxamide;
and pharmaceutically acceptable salts thereof.

5. The method of claim 1, wherein the compound of Formula (I) is (2S)—N-{(1S)-1-cyano-2-[4-(3-methyl-2-oxo-2,3-dihydro-1,3-benzoxazol-5-yl)phenyl]ethyl}-1,4-oxazepane-2-carboxamide:

[chemical structure of the named compound]

or a pharmaceutically acceptable salt thereof.

6. The method of claim 1, wherein the compound of Formula (I) is (2S)—N-{(1S)-1-cyano-2-[4-(3-methyl-2-oxo-2,3-dihydro-1,3-benzoxazol-5-yl)phenyl]ethyl}-1,4-oxazepane-2-carboxamide.

7. The method of claim 1, wherein the composition comprises a pharmaceutically acceptable adjuvant, diluent or carrier.

8. The method of claim 1, wherein administering comprises oral administration.

9. The method of claim 1, wherein the treating comprises decreasing the serum creatinine levels of the patient, as compared to a baseline serum creatinine level measurement taken prior to treatment.

10. The method of claim 1, wherein the treating comprises decreasing the active urinary sediment and/or casts in the patient, as compared to an active urinary sediment measurement taken prior to treatment.

11. The method of claim 1, wherein the treating comprises obtaining an inactive urinary sediment in the patient, defined as less than about 10 red blood cells (RBC) per high power field (HPF).

12. The method of claim 1, wherein the treating comprises decreasing the urinary protein to creatinine ratio (UPCR) in the patient, as compared to an initial UPCR value measured prior to treatment.

13. The method of claim 1, wherein the treating comprises decreasing proteinuria in the patient, as compared to an initial proteinuria measurement in the patient, measured prior to treatment.

14. The method of claim 13, wherein the proteinuria is measured by a urine albumin to creatinine ratio (UACR) or by dipstick urinalysis.

15. The method of claim 1, wherein the treating comprises achieving a complete renal response (CRR) in the patient or a partial renal response (PRR) in the patient.

16. The method of claim 1, further comprising administering one or more additional active agents to the patient in need of treatment.

17. The method of claim 16, wherein the one or more additional active agents comprises a corticosteroid or an immunosuppressant.

18. The method of claim 17, wherein the corticosteroid is a glucocorticoid, and the immunosuppressant is mycophenolate mofetil (MFF) or azathioprine.

19. The method of claim 1, wherein,
$R^1$ is

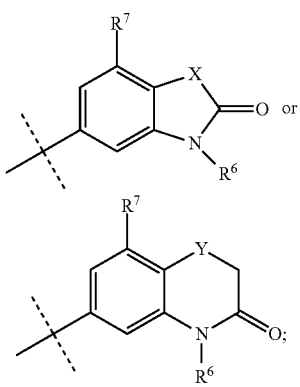

X is O, S or $CF_2$;
Y is O or S;
$R^6$ is $C_{1-3}$alkyl, optionally substituted by 1, 2 or 3 F and optionally by OH, $OC_{1-3}$alkyl, $N(C_{1-3}alkyl)_2$, cyclopropyl, or tetrahydropyran; and
$R^7$ is hydrogen, F, Cl or $CH_3$.

20. The method of claim 19, wherein, X is O; $R^6$ is $C_{1-3}$alkyl, optionally substituted by 1, 2 or 3 F; and $R^7$ is hydrogen.

* * * * *